United States Patent
Rubin et al.

(10) Patent No.: US 11,986,352 B2
(45) Date of Patent: May 21, 2024

(54) ULTRASOUND SPECKLE DECORRELATION ESTIMATION OF LUNG MOTION AND VENTILATION

(71) Applicant: THE REGENTS OF THE UNIVERSITY OF MICHIGAN, Ann Arbor, MI (US)

(72) Inventors: Jonathan M. Rubin, Ann Arbor, MI (US); James D. Hamilton, Marina Del Rey, CA (US); Oliver D. Kripfgans, Ann Arbor, MI (US); J. Brian Fowlkes, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 370 days.

(21) Appl. No.: 17/424,947

(22) PCT Filed: Feb. 5, 2020

(86) PCT No.: PCT/US2020/016790
§ 371 (c)(1),
(2) Date: Jul. 22, 2021

(87) PCT Pub. No.: WO2020/163477
PCT Pub. Date: Aug. 13, 2020

(65) Prior Publication Data
US 2022/0087647 A1    Mar. 24, 2022

Related U.S. Application Data

(60) Provisional application No. 62/801,442, filed on Feb. 5, 2019.

(51) Int. Cl.
*A61B 8/00*    (2006.01)
*A61B 8/08*    (2006.01)
(Continued)

(52) U.S. Cl.
CPC .............. *A61B 8/463* (2013.01); *A61B 8/486* (2013.01); *A61B 8/488* (2013.01); *A61B 8/5207* (2013.01);
(Continued)

(58) Field of Classification Search
CPC ......... A61B 8/463; A61B 8/486; A61B 8/488; A61B 8/5207; A61B 8/5223;
(Continued)

(56) References Cited

U.S. PATENT DOCUMENTS 6,535,835 B1    3/2003    Rubin et al.
7,635,339 B2    12/2009    Harnoncourt et al.
(Continued)

FOREIGN PATENT DOCUMENTS

CN    105611881 A    5/2016
WO    WO-2013/179203 A1    12/2013
(Continued)

OTHER PUBLICATIONS

Goutman et al., Use of angle-independent M-mode sonography for assessment of diaphragmatic displacement, J. Ultrasound Med., 36:1285 (2017).
(Continued)

*Primary Examiner* — Rochelle D Turchen
(74) *Attorney, Agent, or Firm* — MARSHALL, GERSTEIN & BORUN LLP

(57) ABSTRACT

A method of estimating lung motion includes collecting multiple ultrasound image data captured at one or more locations of a sample region of tissue. The method further includes comparing the multiple ultrasound image data and determining temporal correlation coefficients between each of the multiple ultrasound image data. The method still further includes displaying an image of the sample region of the tissue with the temporal correlation coefficients identi- (Continued)

fied, thereby indicating lung motion. In further methods, the determined temporal correlation coefficients are used to determine an amount of decorrelation, which can be used to determine strain of the tissue over the sample region and to calculate lung displacements and lung shape changes representing ventilation.

21 Claims, 22 Drawing Sheets

(51) Int. Cl.
    *G06T 7/00*      (2017.01)
    *G06T 7/254*      (2017.01)

(52) U.S. Cl.
    CPC .......... *A61B 8/5223* (2013.01); *G06T 7/0016* (2013.01); *G06T 7/254* (2017.01); *G06T 2207/10016* (2013.01); *G06T 2207/10136* (2013.01); *G06T 2207/30061* (2013.01)

(58) Field of Classification Search
    CPC ............... G06T 7/0016; G06T 7/254; G06T 2207/10016; G06T 2207/10136; G06T 2207/30061
    See application file for complete search history.

(56) References Cited

U.S. PATENT DOCUMENTS

| | | |
|---|---|---|
| 9,211,110 B2 | 12/2015 | Rubin et al. |
| 9,345,453 B2 | 5/2016 | Rubin et al. |
| 2010/0152580 A1 | 6/2010 | Ganshorn |
| 2013/0046175 A1 | 2/2013 | Sumi |
| 2014/0039313 A1 | 2/2014 | Palti |
| 2016/0095580 A1 | 4/2016 | Rubin et al. |
| 2017/0143289 A1 | 5/2017 | Fouras |
| 2017/0273659 A1* | 9/2017 | Xu .................... G06T 7/174 |

FOREIGN PATENT DOCUMENTS

| | | |
|---|---|---|
| WO | WO-2017/126753 A1 | 7/2017 |
| WO | WO-2017/162860 A1 | 9/2017 |

OTHER PUBLICATIONS

International Application No. PCT/US20/16790, International Search Report and Written Opinion, dated Apr. 27, 2020.

Bouhemad et al. Bedside ultrasound assessment of positive end-expiratory pressure-induced lung recruitment. Am. J. Respir. Crit. Care Med., 183(3):341-7 (2011).

Bouhemad et al. Ultrasound for "lung monitoring" of ventilated patients. Anesthesiology, 122(2):437-47 (2015).

Deninger et al. Quantitative measurement of regional lung ventilation using 3He MRI. Magn. Reson. Med., 48:223-32 (2002).

Ibrahim et al. Lung Ultrasound in Early Diagnosis of Neonatal Ventilator Associated Pneumonia before Any Radiographic or Laboratory Changes. Case Reports in Pediatrics, vol. 2016, Article ID 4168592, 4 pages.

Raimondi et al. Use of neonatal chest ultrasound to predict noninvasive ventilation failure. Pediatrics, 134(4):e1089-94 (2014).

Rubin et al. Potential use of ultrasound speckle tracking for motion management during radiotherapy: preliminary report. J Ultrasound Med. 31(3):469-81 (2012).

Rubin et al. Ultrasound strain measurements for evaluating local pulmonary ventilation. IEEE Int Ultrason Symp. 10.1109/ULTSYM.2015.0181 (2015).

Wang et al. Lung ultrasound: a promising tool to monitor ventilator-associated pneumonia in critically ill patients. Crit. Care. 20(1):320 (2016).

Zhou et al., 3-D Velocity and Volume Flow Measurement In Vivo Using Speckle Decorrelation and 2-D High-Frame-Rate Contrast-Enhanced Ultrasound, IEEE Transactions on Ultrasonics, Ferroelectrics, and Frequency Control, 65(12): 12 pages (2018).

* cited by examiner

Correlation values in selected region for:
apex - regular breath - 4 sec.dcm:
Lag = 1    Correlation = 0.83
Lag = 2    Correlation = 0.63
Lag = 3    Correlation = 0.49

US 11,986,352 B2

ULTRASOUND SPECKLE DECORRELATION ESTIMATION OF LUNG MOTION AND VENTILATION

CROSS-REFERENCE TO RELATED APPLICATIONS

This application is a US national phase of PCT/US20/16790, filed Feb. 5, 2020, and claims the benefit of U.S. Provisional Application Ser. No. 62/801,442, filed Feb. 5, 2019, the entirety of which is hereby incorporated herein by reference.

FIELD OF THE DISCLOSURE

The present disclosure relates generally to techniques for estimating lung motion and ventilation and, more particularly, to techniques for estimating lung motion and ventilation using decorrelation determinations.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Respiratory problems can be particularly harmful to patients and can produce lasting deleterious effects. For example, respiratory failure is common with premature births and is a leading cause for the prevalence of ventilatory assistance among infants. For adults, respiratory issues can affect the heart, muscles, and bones. Patients can exhibit shortness of breath, changes to skin, arrhythmias, and loss of consciousness, in some cases.

There are numerous techniques for trying to assess lung performance. These include techniques for assessing inhalation and exhalation motion of the lung, as well as oxygen volumes for each. Commonly, to measure respiratory function, pulmonary function tests are performed, where a patient breathes into a tube and the clinician measures the volume of oxygen during inhalation and exhalation. The techniques are, however, inexact. Other techniques have examined the lung surface and measured for strain at the lung surface using speckle tracking, as a way of assessing lung condition. Strain is, in some sense, the perfect metric, since strain is positive during inspiration and negative during expiration. However, there are difficulties with the strain metric when applied to humans. One overarching problem in humans is that when the moving lung moved under ribs, the surface could no longer be tracked. Furthermore, local strain measurements may not work on certain body types, such as people with more subcutaneous fat/tissue, making speckle analysis very difficult.

Therefore, while there is considerable interest in measuring local lung ventilation, past ultrasound techniques that use speckle tracking to measure strains along the lung surface during respiration are somewhat limiting.

SUMMARY OF THE INVENTION

In accordance with an embodiment, a method of estimating lung motion, the method comprises: collecting multiple ultrasound image data captured at one or more locations of a sample region of tissue; comparing the multiple ultrasound image data and determining temporal correlation coefficients between each of the multiple ultrasound image data; and displaying an image of the sample region of the tissue with the temporal correlation coefficients identified thereby indicating lung motion.

In some embodiments, the method includes: collecting the multiple ultrasound image data at a plurality of locations of the sample region; and comparing the multiple ultrasound image data and determining temporal correlation coefficients for each of the plurality of locations of the sample region.

In some embodiments, the method includes identifying a surface of the sample region based on the determined temporal correlation coefficients.

In some embodiments, the method includes identifying an internal structure of the sample region based on the determined temporal correlation coefficients.

In some embodiments, collecting the multiple ultrasound image data captured at the one or more locations of the sample region of tissue comprises collecting multiple ultrasound image data captured from a 1D ultrasound probe, a 2D ultrasound probe, or a 3D ultrasound probe, or a 4D ultrasound probe.

In some embodiments, collecting the multiple ultrasound image data captured at the one or more locations of the sample region of tissue comprises collecting multiple ultrasound image data captured from a plurality of ultrasound probes.

In some embodiments, the method includes determining the temporal correlation coefficients between each of the multiple ultrasound image data at different successive lag times.

In some embodiments, the method includes determining from the temporal correlation coefficients regions within the sample region that demonstrate no motion.

In some embodiments, the method includes: determining decorrelation using two different beam correlation widths; and calculating lung displacements and lung shape changes representing ventilation from the two different beam correlation widths.

In some embodiments, the method includes identifying local displacements and ventilation by determining amounts of decorrelation for two different beam correlation widths or point spread functions.

In some embodiments, the amounts of decorrelation for two different beam correlation widths or point spread functions are determined using:

$$TD(i) = (LD/(PSF(i))) + SD$$

$$TD(j) = (LD/(PSF(j))) + SD$$

where TD (i) and TD (j) are the total decorrelation for the ith sampling and jth sampling, respectively, PSF (i) and PSF (j) are the point spread function during the ith sampling and jth sampling, respectively, LD is the lung surface displacement during the sampling period, which is constant, and SD is the shape induced decorrelation during the same period.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIGS. 5-15 illustrate various images and plots of decorrelation determinations, in accordance with various examples as described.

FIGS. 8A, 8B, and 9 illustrate similar image and plot to that of FIGS. 7A and 7B, but after adding low pass filtering of correlation values between firings, showing reducing variation. As shown, determining minimum correlation to assess lung motion magnitude due to correlation noise is still a challenge. As also illustrated in FIG. 9, other lags result in greater decorrelation with increasing lag at times of lung motion. In this example, a lag of >1 appears to provide improved distinction between moving and not moving lung.

FIGS. 10A and 1013 illustrate example image and plot for a lag=2, image and plot, respectively.

DETAILED DESCRIPTION

Figure 1:
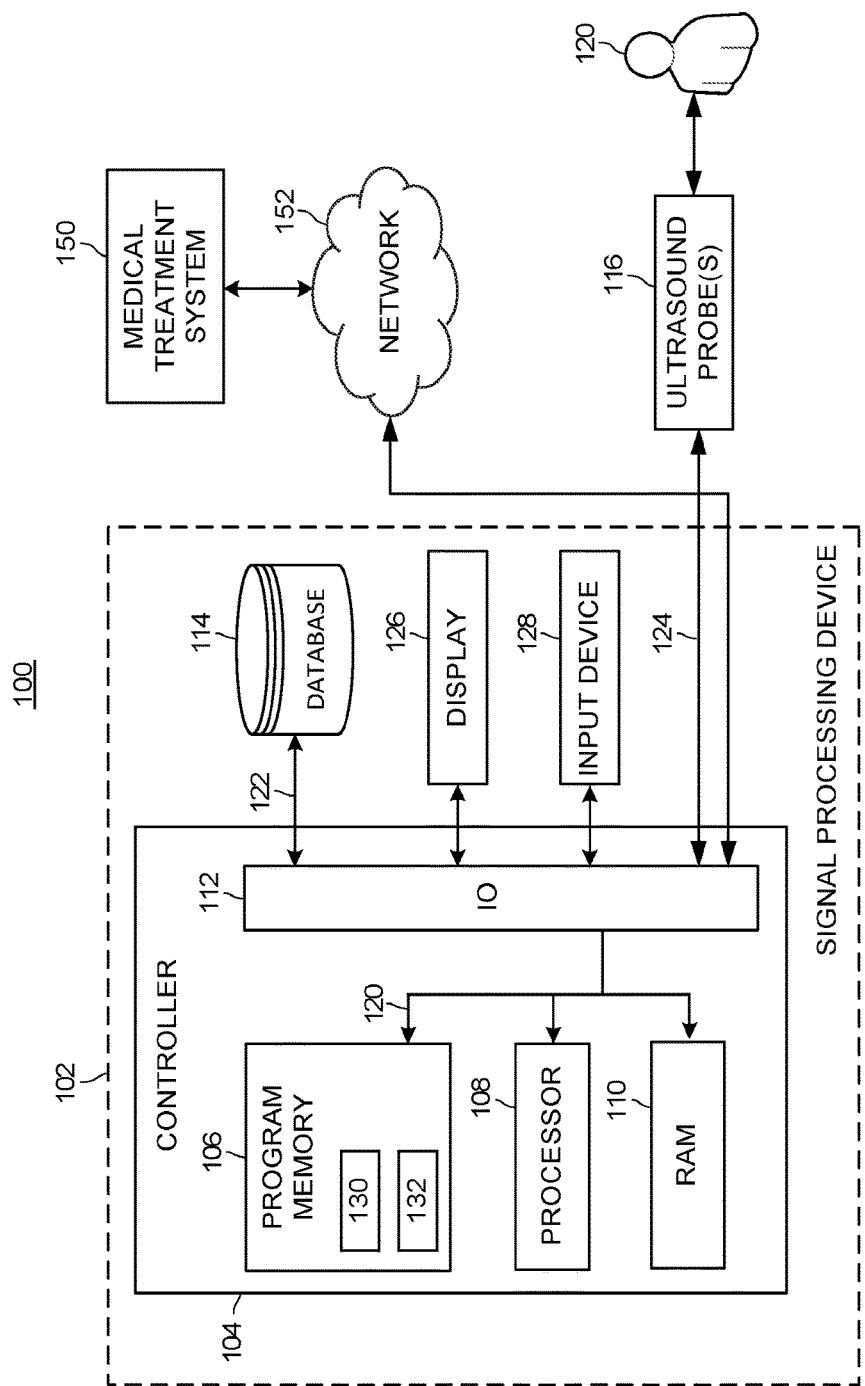
FIG. 1 illustrates an ultrasound imaging system configured to assess lung performance using decorrelation determinations, in accordance with an example.

The present application describes techniques to measure local lung ventilation and lung motion using decorrelation and decorrelation rates of one or more ultrasound images of the lung surface.

Ultrasound imaging and measurement of the lung surface is difficult since the lung surface produces reflected signals that can have large contributions of noise and artifact. Ultrasound signals do not enter normal lung tissue, so any signal projecting into the lung on an ultrasound image is produced by multiple reflections at, and from, the most superficial lung/soft-tissue boundary. With the present techniques, we demonstrate that ultrasound signals can nonetheless be compared at different times and at different locations to assess local motion and local displacement of the lung surface. More specifically, the present techniques determine decorrelations between ultrasound image data and use these decorrelations to assess the lung, for example, to assess lung motion and ventilation. The present techniques utilize the fact that decorrelation is dependent on tissue motion and structure. The present techniques assess regional lung motion by measuring the decorrelation of ultrasound signals with time. For example, the detected scattered ultrasound signals from a beam repeatedly transmitted at the same location (i.e., M-mode acquisition) can be compared using decorrelation to assess the tissue motion between beam transmission times.

In various examples, the present techniques assess the underlying condition of the lung based on the amount of signal decorrelation between ultrasound image data. If there is underlying structure in the lung visible to an ultrasound beam, such as pneumonia or pulmonary edema, the amount of decorrelation will change compared to a healthy lung, producing a very distinctive, variation in beam (i.e., M-mode) decorrelation over time, thus allowing for the identification of these internal structures.

This method can be modified by using real-time 2D ultrasound images to obtain multiple M-mode lines that can be imaged to improve the signal to noise of the method.

Applying decorrelation-based approaches, the present techniques are able to distinguish between moving and non-moving targets within lung tissue. For example, the present techniques may identify structure based changes in correlation status. A moving, internal, pulmonary structure in the lung may go from decorrelating to recorrelating with a prior M-mode firing, when the pulmonary structure moves across the ultrasound beam, during the respiratory cycle. That is, the M-mode signal matches a past M-mode signal because the structure has returned to the previous (past) position due to respiratory or other motion. Non-moving targets, by contrast, targets such as pneumothoraces, will remain fully correlated throughout the respiratory cycle. By measuring and determining changes in correlation states, the type of target in the lung tissue may be identified.

These techniques can be used to determine lung motion and deformation. Lung deformation is directly related the expansion and contraction of the lung surface and reflects local ventilation function. For example, lung surface motion can decorrelate based on pure lung translation and due to shape changes of the lung surface, like expansion and contraction, produced by ventilation, i.e. inhalation and exhalation. Lung tissue that is either collapsed or contains non-gas exchanging materials like fluids in pneumonia or pulmonary edema will not ventilate. These two components of decorrelation can be separated by sampling the motion of the lung surface with two different beam geometries. Translation induced decorrelation rates will change with different beam point spread functions (beam widths), but local ventilation induced decorrelation changes depend on deformation, and decorrelation produced by this change in shape will not change with changes in point spread function. This can be simply seen in the following two equations where TD (i) is the total decorrelation for the $i^{th}$ sampling, PSF (i) is the point spread function during the $i^{th}$ sampling, LD is the lung surface displacement during the sampling period, which is constant, and SD is the shape induced decorrelation during the same period.

$$TD(i) = \left(\frac{LD}{PSF(i)}\right) + SD \quad (1)$$

$$TD(j) = \left(\frac{LD}{PSF(j)}\right) + SD \quad (2)$$

These are two equations and two unknowns, which can be solved for the lung displacement (LD) and shape decorrelation (SD).

This could be further modified in the lung bases adjacent to the liver. Since the liver translates with breathing but barely deforms, one could measure the decorrelation in the liver and compare it to the lung. The liver decorrelation would reflect the LD in the LD/PSF (i) component of equations 1 and 2. This would permit a determination of ventilation or SD without requiring two PSF's. Since the speckle in the liver is very stable and easy to track, in some examples, the ultrasound system directly measures LD in the liver and uses that to estimate LD in the lung base. Such examples would also only use a single PSF. The publication, Goutman S A, Hamilton J D, Rubin J M, Use of angle-independent M-mode sonography for assessment of diaphragmatic displacement, J. Ultra Med. 2017; 36:1285, is hereby incorporated by reference in its entirety.

In some examples, the present techniques determine motion of the lung surface and internal structures based on beam geometry patterns and ultrasound slow time rates, which will represent the times between firings. Using these characteristics, the present techniques determine the speed with which the local lung surface is moving, and by comparing different regions, the present techniques estimate relative motions and lung features, such as strain.

The present techniques may be implemented with various types of ultrasound transducers. In some examples, a single element transducer device may be used. In some examples, a multi-element transducer array device may be used. The present techniques may include generating ultrasound images displaying lung surface, internal features, etc. on a digital display, such as on a portable computer, tablet PC, smart phone, etc.

In various examples, the ultrasound image data is generated using one or more 1D, 2D, or 3D ultrasound transducer probes to collect ultrasound images. In various examples, the ultrasound images are M-mode (motion) images, B-mode images (2D and 3D brightness mode images), A-mode traces or plots, Doppler mode images, M-mode lines, RF (radiofrequency) lines, and RF images (e.g., spatially distributed RF lines). Multiple transducer elements or multiple transducer arrays may be distributed on a subject around the sample region of interest. In some examples, one or more transducer elements or arrays may include piezoelectric elements. In another example, the difference between decorrelating signals are used to estimate local strain for comparison purposes.

FIG. 1 is an example block diagram of an example lung motion and ventilation analysis system 100, illustrating the various components used in implementing an example embodiment of an ultrasound imaging system. A signal-processing device 102 (or "signal processor") may be configured to examine a patient 120 via one or more wearable ultrasound probes 116 in accordance with executing the functions of the disclosed embodiments. The signal-processing device 102 may have a controller 104 operatively connected to the database 114 via a link 122 connected to an input/output (I/O) circuit 112. It should be noted that, while not shown, additional databases may be linked to the controller 104 in a known manner. The controller 104 includes a program memory 106, one or more processors 108 (may be called microcontrollers or a microprocessors), a random-access memory (RAM) 110, and the input/output (I/O) circuit 112, all of which are interconnected via an address/data bus 120. It should be appreciated that although only one processor 108 is shown, the controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124, which may include one or more wired and/or wireless (Bluetooth, WLAN, etc.) connections, may operatively connect the controller 104 to the ultrasound probe(s) 116 through the I/O circuit 112. The ultrasound probe(s) 116 may be operatively connected to the patient 120 at a location corresponding to a sampling region of the patient.

The program memory 106 and/or the RAM 110 may store various applications (i.e., machine readable instructions) for execution by the processor 108. For example, an operating system 130 may generally control the operation of the signal-processing device 102 and provide a user interface to the signal-processing device 102 to implement the processes described herein. The program memory 106 and/or the RAM 110 may also store a variety of subroutines 132 for accessing specific functions of the signal-processing device 102. By way of example, and without limitation, the subroutines 132 may include, among other things: a subroutine for capturing ultrasound images of a patient, a subroutine for filtering captured ultrasound images, a subroutine for determining correlation coefficients between captured ultrasound image data (e.g., frames or lines), a subroutine for determining correlation coefficients at different sampled locations of a tissue or organ, a subroutine for determining lung performance from the correlation coefficients, such as lung motion or lung ventilation, and a subroutine for displaying determined lung performance.

The subroutines 132 may also include other subroutines, for example, implementing software keyboard functionality, interfacing with other hardware in the signal-processing device 102, etc. The program memory 106 and/or the RAM 110 may further store data related to the configuration and/or operation of the signal-processing device 102, and/or related to the operation of the one or more subroutines 132. For example, the ultrasound image data may be data gathered by the probe(s) 116, data determined and/or calculated by the processor 108, etc. In addition to the controller 104, the signal-processing device 102 may include other hardware resources. The signal-processing device 102 may also include various types of input/output hardware such as a visual display 126 and input device(s) 128 (e.g., keypad, keyboard, etc.). In an embodiment, the display 126 is touch-sensitive, and may cooperate with a software keyboard routine as one of the software routines 132 to accept user input. It may be advantageous for the signal-processing device 102 to communicate with a broader medical treatment system 150 through a network 152, using any of a number of known networking devices and techniques (e.g., through a computer network such as a hospital or clinic intranet, the Internet, etc.). For example, the ultrasound processing system may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Figure 2:
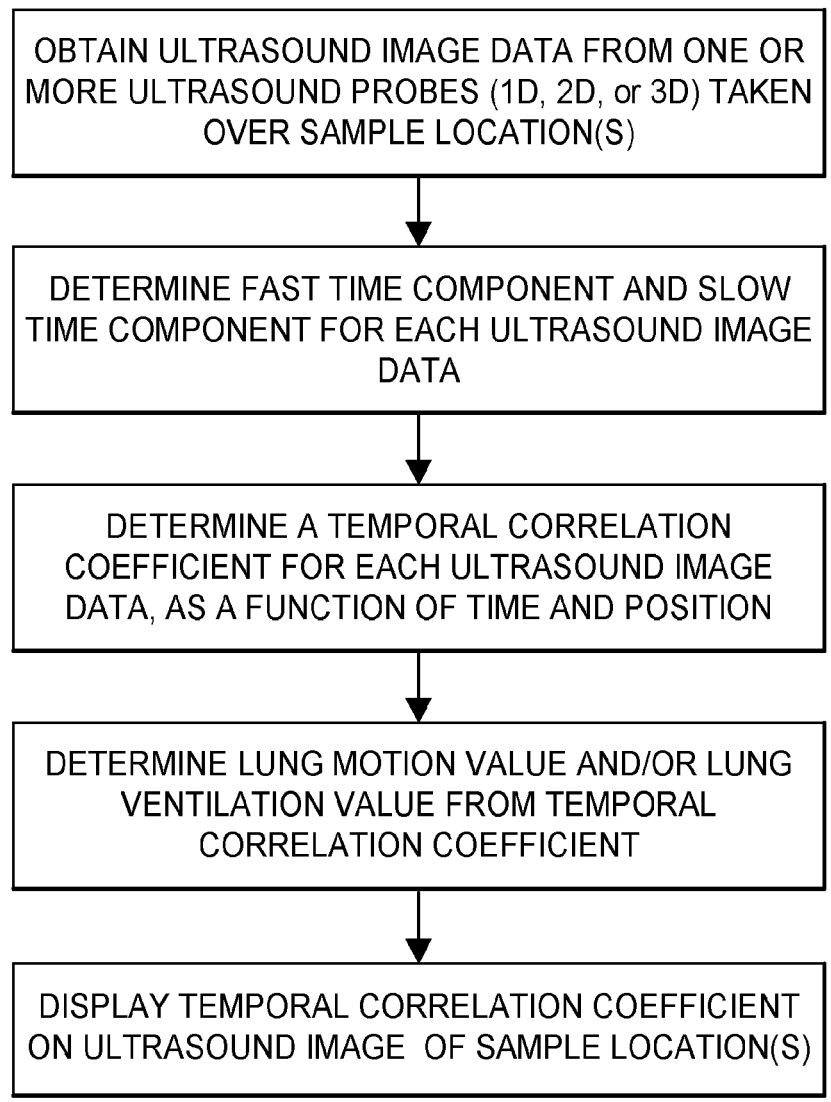
FIG. 2 illustrates a process of decorrelation-based lung performance assessment as may be implemented by the process of FIG. 1, in accordance with an example.

FIG. 2 illustrates an example method for assessing lung tissue. A plurality of ultrasound images are captured from one or more ultrasound probes placed on a subject to capture images of a sample region. These ultrasound images contain ultrasound image data. In this example, the ultrasound image data contains fast time component data and slow time component data (i.e., spatial and temporal data), both of which are determined for each ultrasound image. From the fast and slow time components, temporal correlation coefficients are determined for each ultrasound image as a function of time and position. These temporal correlation coefficients represent lung surface motion and are compared across ultrasound images to determine lung surface deformations corresponding to ventilation.

In an example implementation, an ultrasound data image taken using repeated beam acquisitions at the same location (i.e., M-mode) or extracted B-mode image columns, may be expressed as an ultrasound signal $s_i(x,m)$, where the sample along the beam is denoted by subscript i (i.e., fast time), x is the beam location, and m is the acquisition number (i.e., slow time). This ultrasound signal will have a fast time and slow time component. Then the temporal correlation coefficient, $\rho$, between ultrasound acquisitions at beam (or column) location x and beam sample $i_o$ is:

$$\rho(x, i_o, l) = \frac{1}{W} \sum_{i=i_o-W/2}^{i_o+W/2} \frac{\tilde{s}_i(x, m)\tilde{s}_i(x, m+l)}{\sigma(x, m)\sigma(x, m+l)},$$

where W in the correlation window size in beam samples and l is the acquisition lag. $\tilde{s}_i(x, m)$ is the mean subtracted ultrasound signal and cs is the standard deviation over the correlation window. The local correlation coefficient for fixed acquisition lag (e.g. l=1) $\rho(x, i_o, 1)$, or decorrelation coefficient, $1-\rho(x, i_o, 1)$, is what is measured and displayed, by the ultrasound imaging system. For correlation M-mode images, each pixel in the image represents the correlation value taken over the window for which that pixel is in the center of the window.

Ultrasound data may be processed to improve measurement of lung surface motion. For example, the ultrasound data may be temporally high pass or band pass filtered to reduce the signal components from stationary and slow moving echoes of the ultrasound data. For lung surface imaging using ultrasound, this can significantly reduce the specular reflections from the lung. These signal components can produce error in lung motion measurement because they present as stationary structures, which are mixed with the desired motion signals from the lung surface. Other forms of signal processing of ultrasound data may also be used, such as spatial (e.g., across beam) filtering and downsampling (reducing number of samples) or combinations thereof.

The correlation or decorrelation signals can be filtered. In some examples, temporary low pass filtering may be applied to a time series of correlation measurements from an acquisition location to reduce high frequency correlation noise. This can improve signal quality because the ultrasound data acquisition rate, and therefore the correlation measurement rate, is typically significantly higher than the lung motion (respiratory) rate.

The method of FIG. 2 can be implemented using multiple ultrasound detectors or a single ultrasound detector, such as a portable detector carried in an operator's pocket. Because correlation coefficients are determined and used for assessment, the limitations of speckle tracking strain-based techniques may be overcome. The present techniques are more noise resistant and not affected by rib shadowing because there is no tracking involved.

With these correlation coefficients, the ultrasound system can compare them for different regions of the lung and determine the decorrelation of the lung surface (e.g., of the speckle from the lung surface) as that surface moves through an ultrasound beam. The larger the decorrelation, the faster the surface is moving. Further, recorrelation of the ultrasound signal after a sufficient time delay is evidence for a relatively stable, underlying structure produced by pulmonary consolidation or pulmonary edema. Therefore, this is a quantitative measure that can be used to measure lung motion, ventilation, and lung structure. Decorrelation has a further advantage in that it is not directionally dependent and can measure all components of motion, unlike speckle tracking motion measurement, which cannot measure motion that is not in image plane. Out of plane motion also degrades in-plane motion measurements. Decorrelation reflects all the motion, so as long as the beam geometry is isotropic, and as result preferential motion directions are accounted for with the present techniques.

The present techniques can distinguish deep inhalations and exhalations from normal, smaller inhalations and exhalations. Moreover, positional variations in lung surface motion across the lung can be measured. By performing decorrelation measurements at different sample regions, a more accurate assessment of lung motion and ventilation can be determined. It is well known that the base of the lung is ventilated more than the apex, which we can see in variations in decorrelations. As a result, in some examples, the present techniques are able to measure spatial derivatives of decorrelation, where these derivatives will reflect inhalation and exhalation, similar to strain-based measures. Further still, with the present techniques we have observed that the areas under the decorrelation curve with time are equal in inhalation and exhalation. This is a very compelling result because due to conservation of lung volume/mass, the amount of gas exhaled must equal that inhaled. If not the lungs would ultimately collapse or explode. Yet, further still, these areas can be subdivided on exhalation in order to be compared to a standard pulmonary function test known as forced expiratory volume in 1 sec. In this test, a subject exhales forcibly, and the fraction of the exhalation that occurs in the first second, reflects underlying lung function/disease. The normal ratio is >80%. We can do the same thing with decorrelation area where we see the portion of the total decorrelation area that occurs in the first 1 second.

Figure 3:
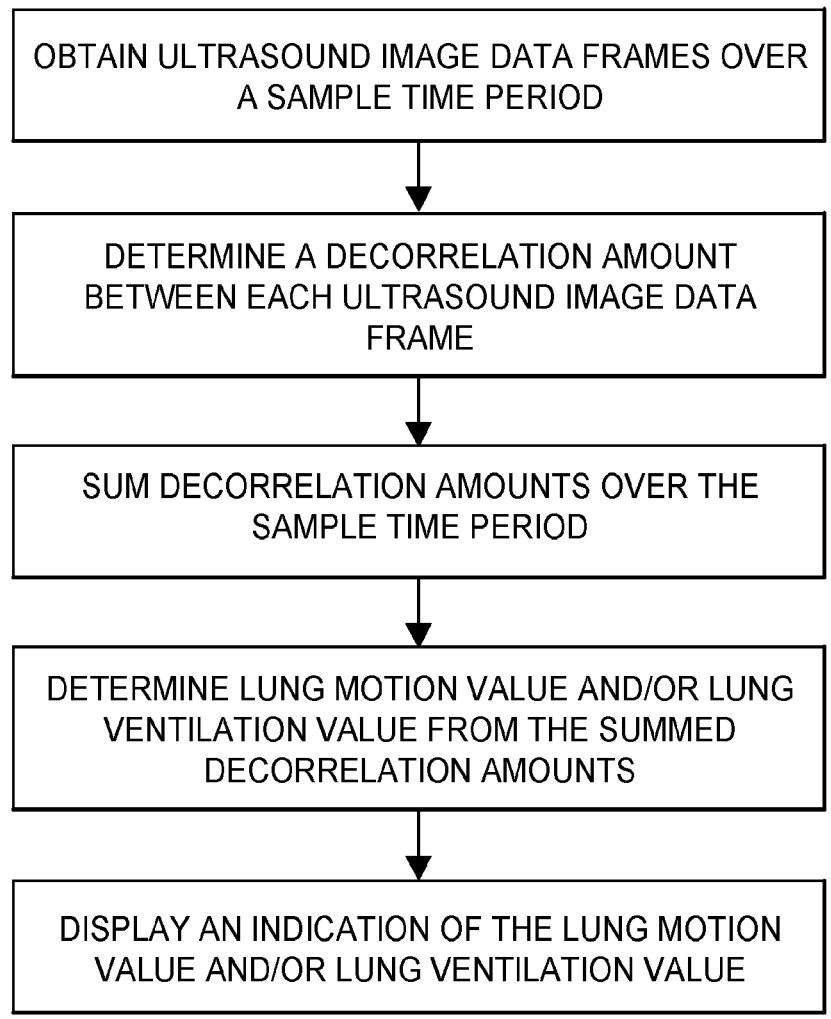
FIG. 3 illustrates a process of decorrelation-based lung performance assessment as may be implemented by the process of FIG. 1, in accordance with another example.

FIG. 3 illustrates another example method. Ultrasound image data frames are obtained over a sample period. A decorrelation amount is determined between each adjacent data frame, although any time lag could be used if the results would be of interest. These decorrelation amounts are summed over a sampling period of time. The lung motion or lung ventilation is determined from this summed value, and ultrasound image data is displayed as a result.

Figure 4:
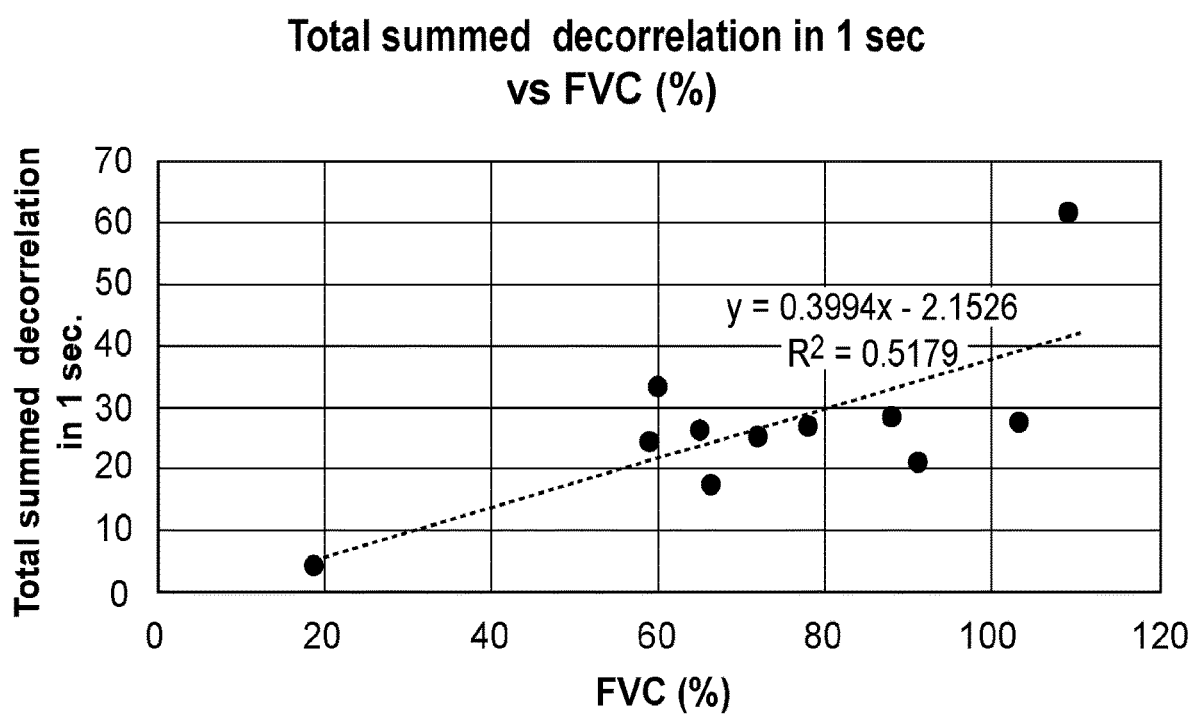
FIG. 4 illustrates a plot of total summed decorrelation over a sample time frame, in an example implementation of the process of FIG. 3.

FIG. 4 illustrates a plot of decorrelation values, in accordance with an example implementation of the method of FIG. 3. What is being measured and plotted is the sum of the frame to frame decorrelation at the sampling site on the lung surface over a period of one second during breathing. For instance if the sampling is at 70 frames per second, this would be the following sum: (Decorrelation between frame 1 and 2)+(decorrelation between frame 2 and 3)+(decorrelation between frame 3 and 4)+ . . . +(decorrelation between frame 69 and 70)=total summed decorrelation. So if the decorrelation is a constant 0.5, i.e. 0.5 between all frame pairs, that would represent a total value of (70−1) pairs*0.5=34.5. If one knows the point spread function of the ultrasound beam or calculates it from the image, this value would correspond to lung displacement. In an example implementation, this type of conversion is performed and used to produce measurements of lung motion in cm, for example. In the illustrated example, the x-axis is forced vital capacity which is the volume of air that a subject can exhale in a forced breath. The units are percentages based on the amount of gas that is exhaled compared to a population of 3,600 subjects aged 4-80 years, for example purposes. It is clear that the sum decorrelation value correlates with FVC.

FIGS. 5A-15C illustrate example implementations of techniques herein.

Figure 5A:
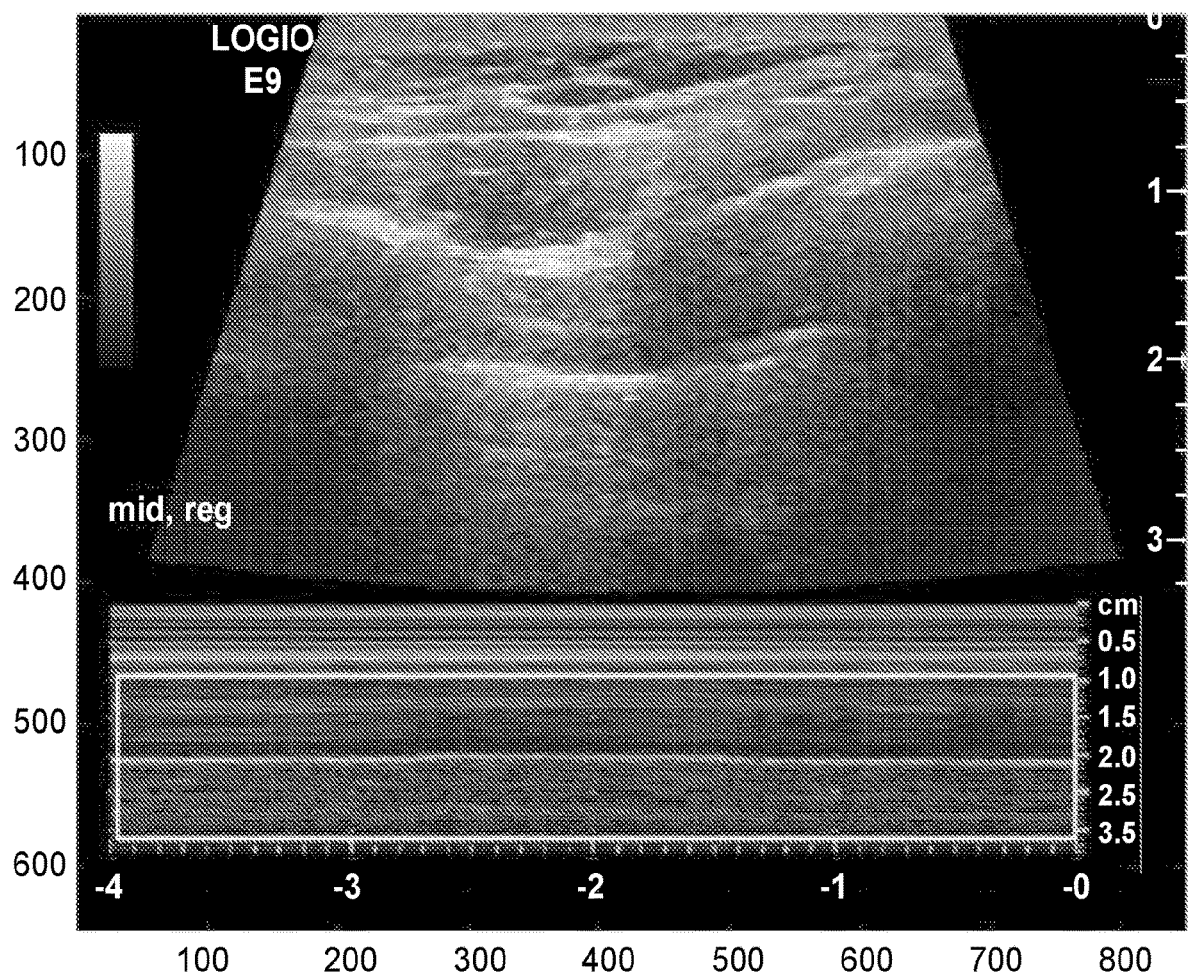
FIGS. 5A and 5B illustrate example analysis of mid level, normal breath, 4 sec M mode, with original DICOM image and M=mode subset showing extracted M mode data.
Figure 5B:
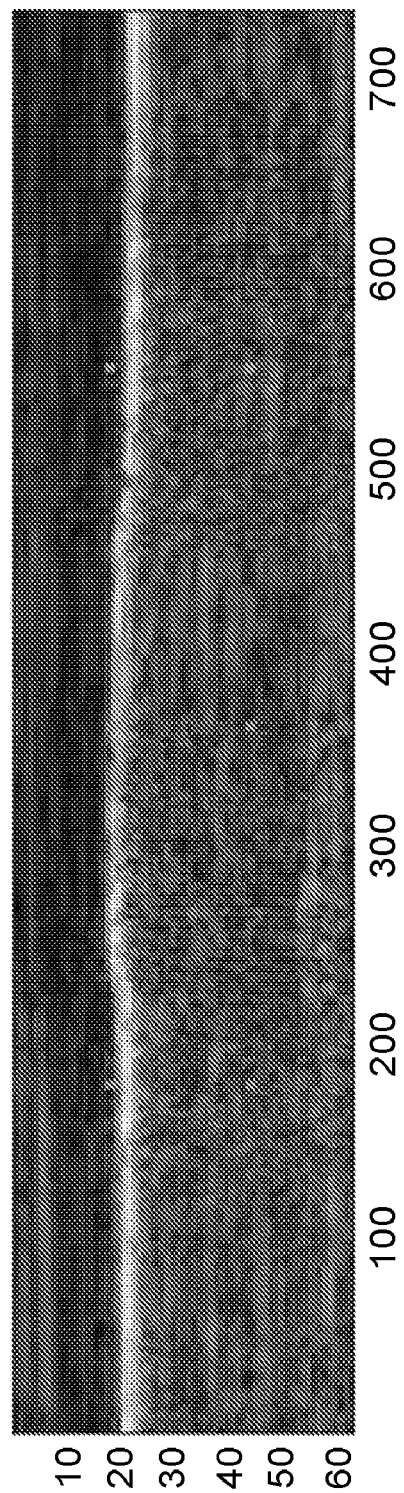
Figure 6A:
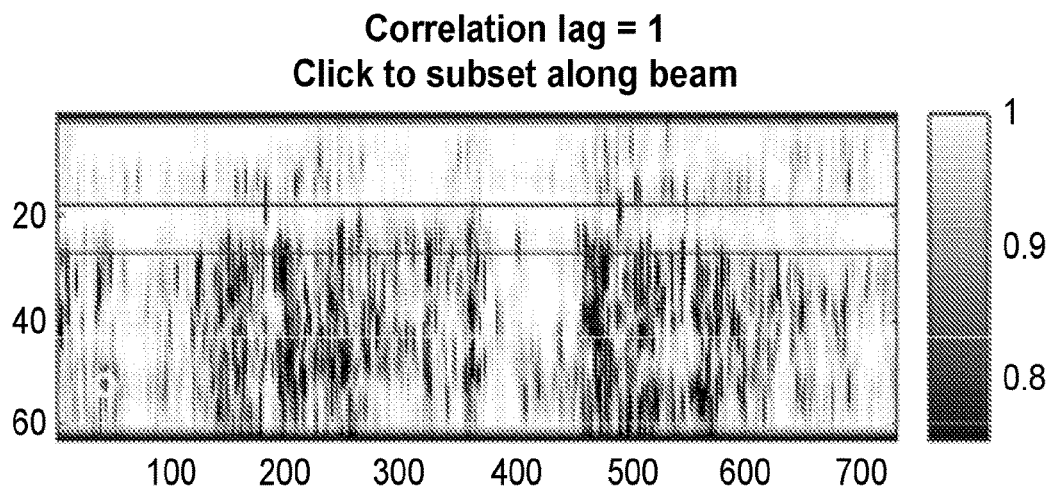
FIGS. 6A and 6B illustrate correlation between M mode firings and provide a plot of average correlation between blue lines, corresponding to at the lung surface.
Figure 6B:
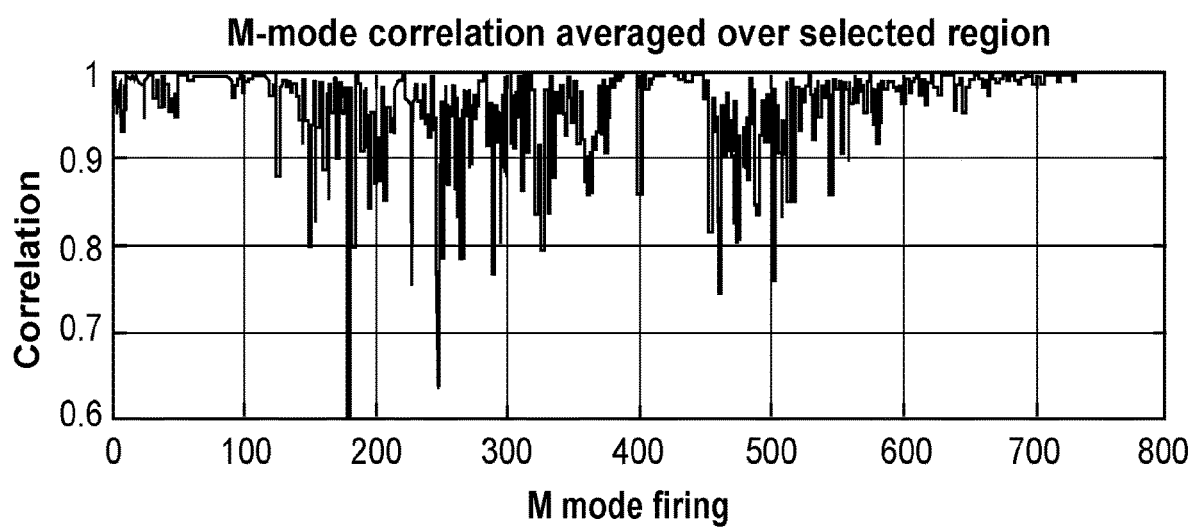
Figure 7A:
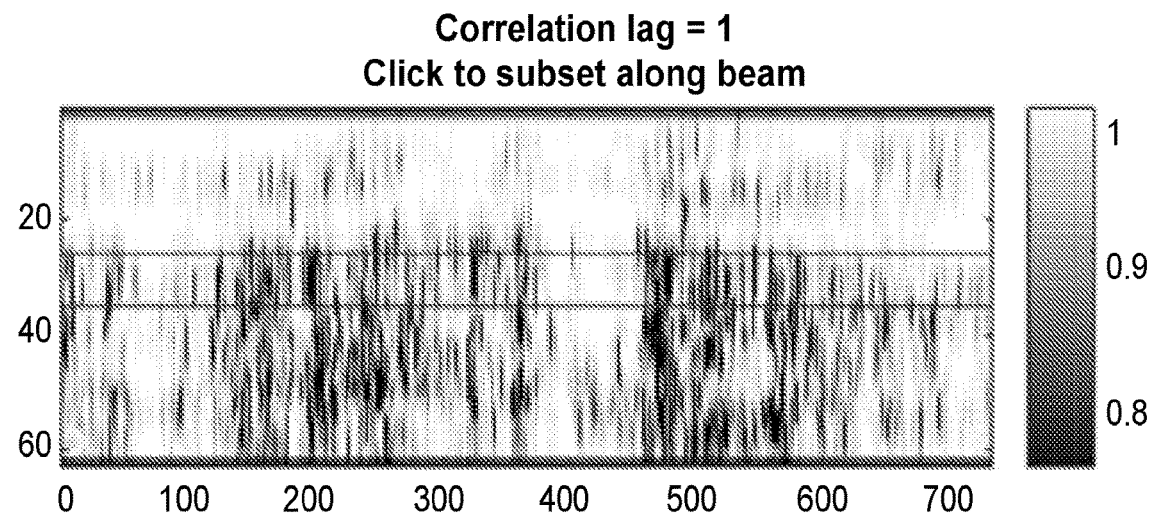
FIGS. 7A and 7B illustrate a similar image and plot to that of FIGS. 6A and 6B, but after selecting a new region, just below the lung surface, away from specular reflection region. Correlation lower with more variation at firing times when lung is moving, is shown. Breath is at full exhale or inhale at firing approximately 75 and 410, as shown.
Figure 7B:
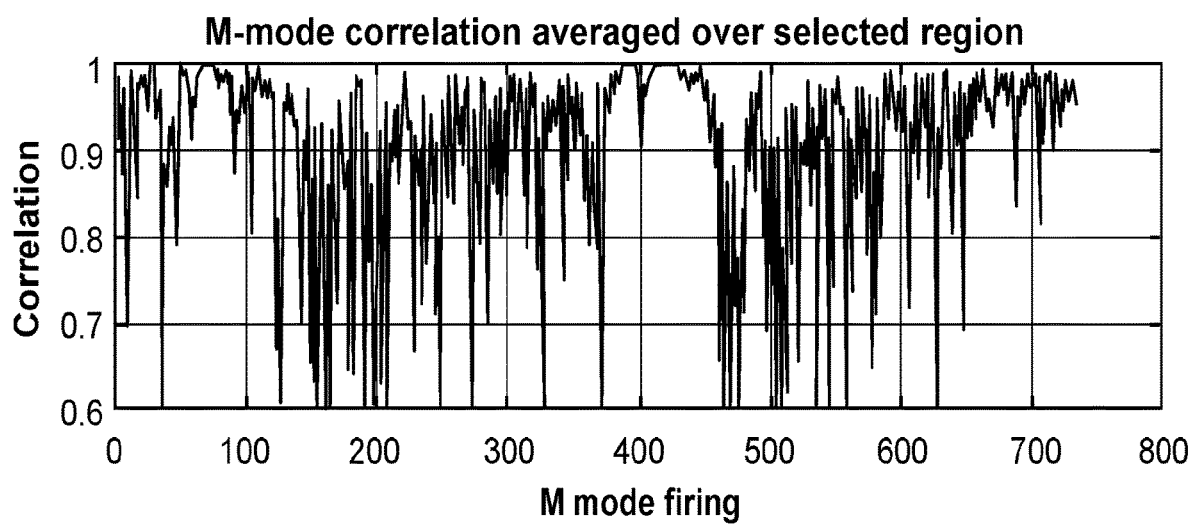

FIG. 5A illustrates an M-mode ultrasound image taken at a mid-level sampling region of the lung, during normal breath, using a 4 sec M-mode. FIG. 5A illustrates the original DICOM image and M-mode subset. FIG. 5B illustrates extracted M-mode data. FIG. 6A illustrates a correlation between M-mode firings for the image data from FIGS. 5A and 5B, and showing a selected region of interest in FIG. 5A ranging from 1.0 cm to 3.0 cm between the skin surface. The bright line in the M-mode at 2.0 cm represents the lung surface. FIG. 6B is a plot of the average correlation between the two lines in FIG. 6A, which corresponds to the lung surface. FIG. 7A illustrates the same plot of FIG. 6A, but taken over a new region, just below the lung surface, away from the speckle reflection region. FIG. 7B illustrates the average correlation between the two lines of FIG. 7A, showing a lower correlation with more variation at firing times when the lung is moving. Here the breath is at full exhale or inhale at firing approximately 25 and 410, in the x-axis.

Figure 8A:
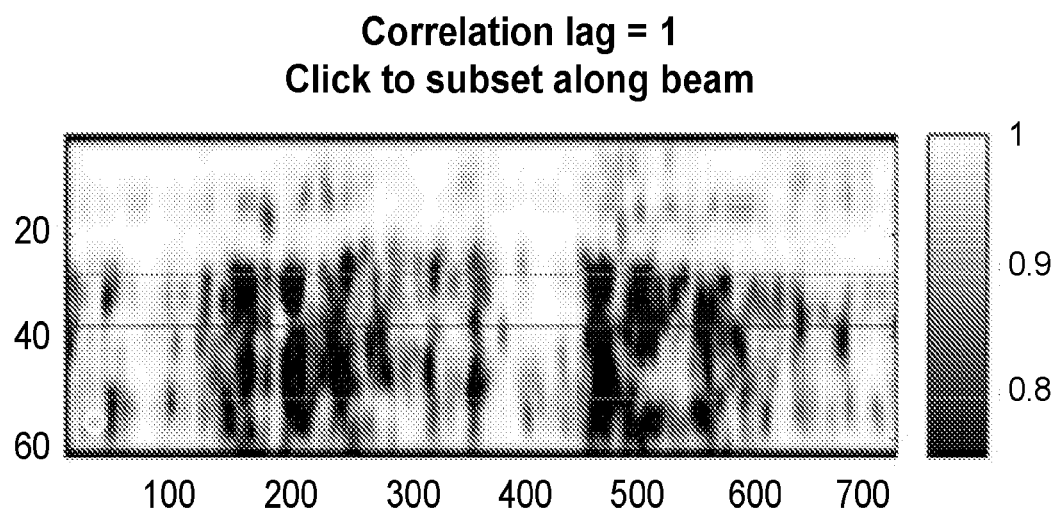
Figure 8B:
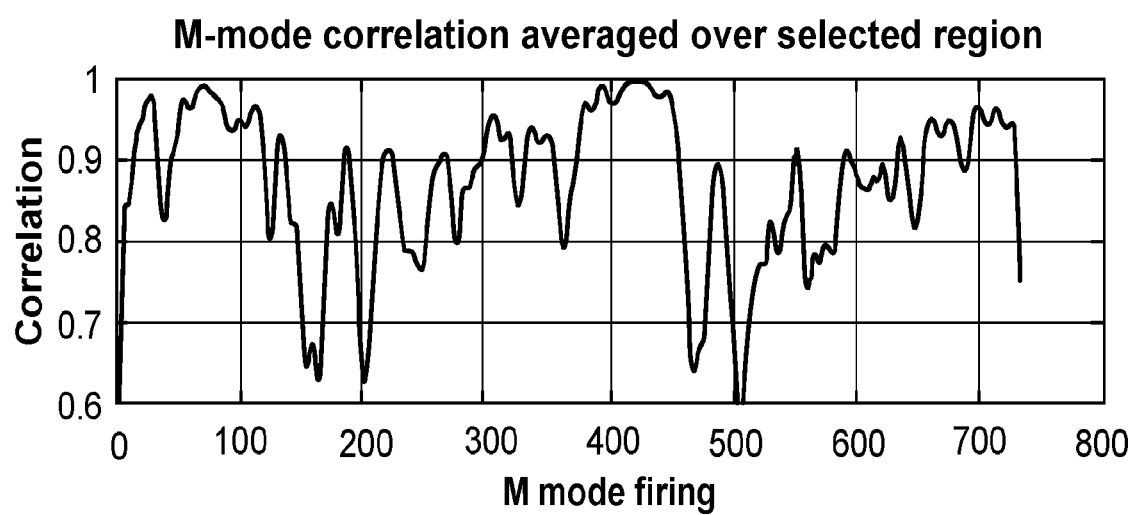

FIGS. 8A and 8B illustrate similar data to FIGS. 7A and 7B, but after low pass filtering of correlation values between firings has been applied. The result is reduced variation.

Figure 9:
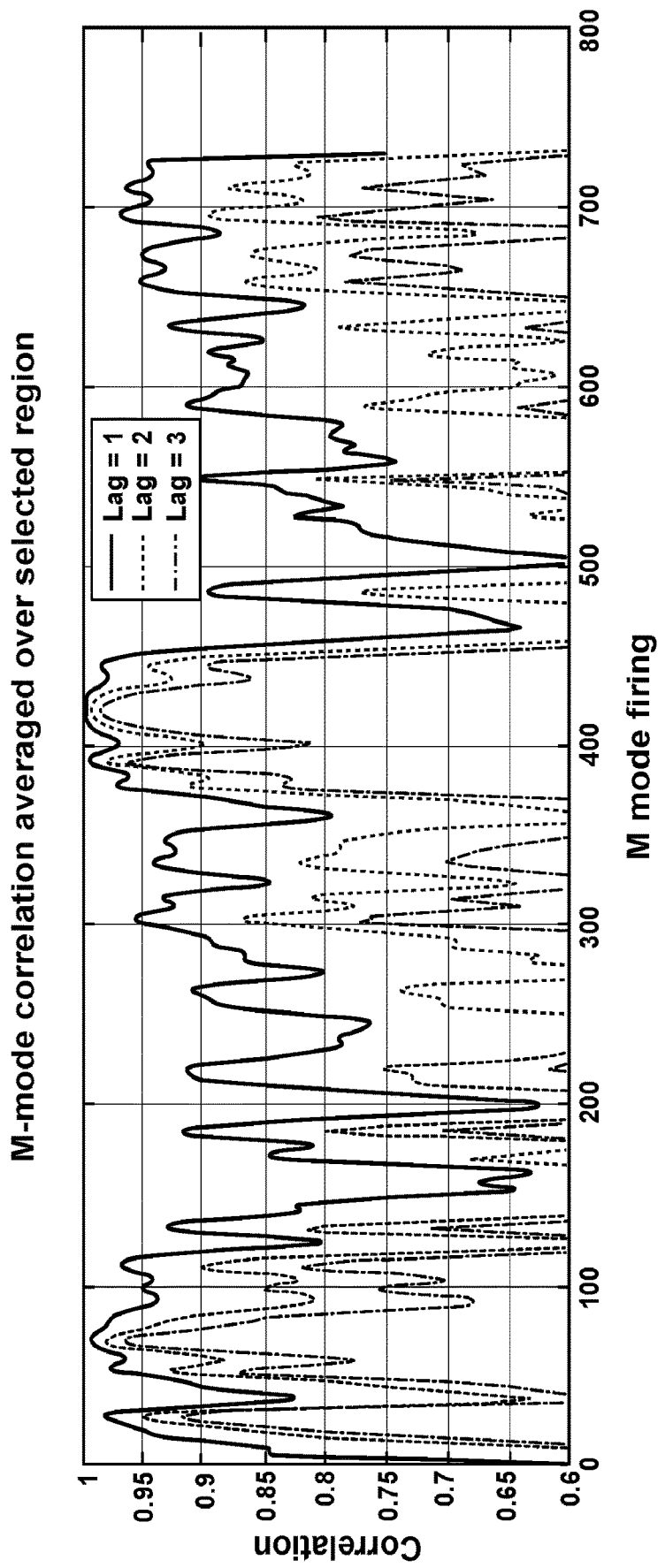
Figure 10A:
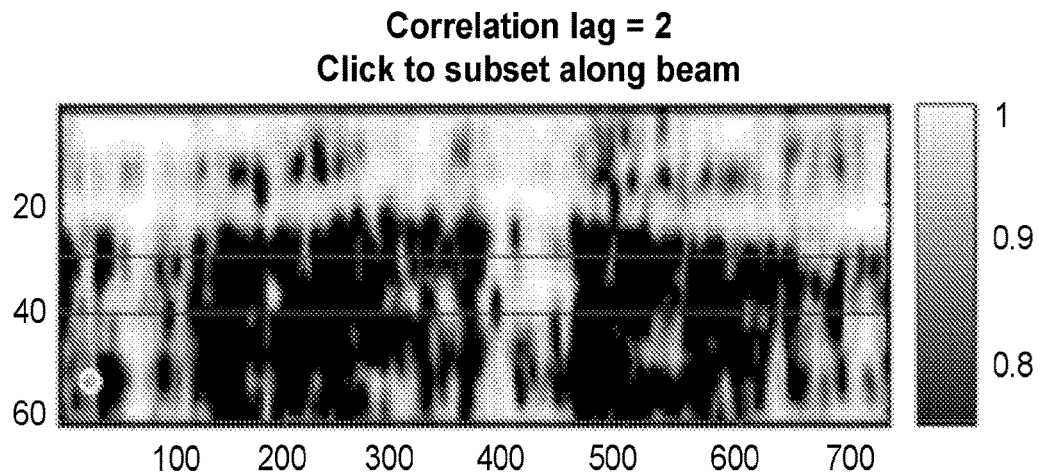
Figure 10B:
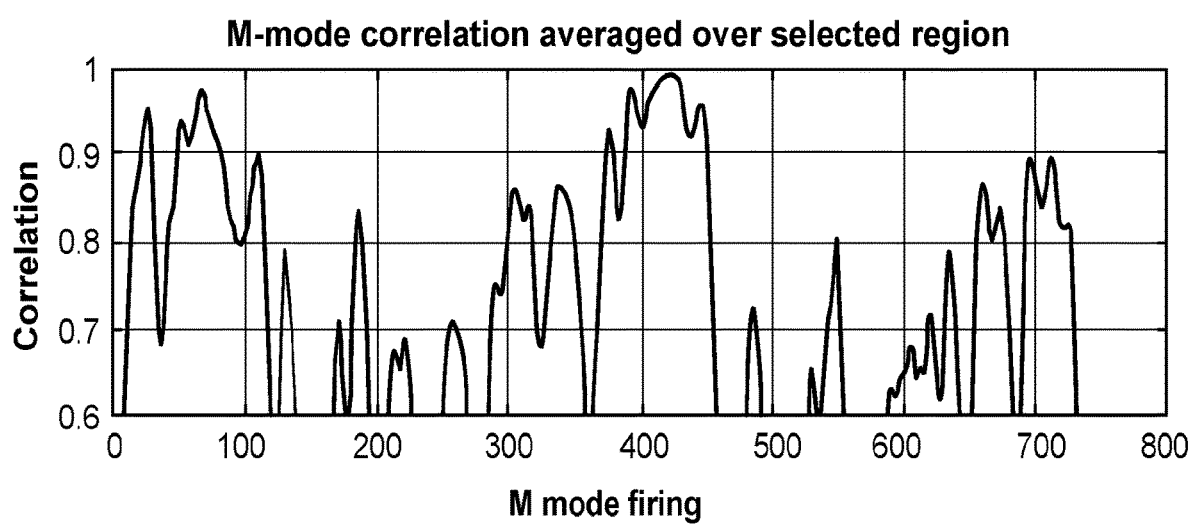

FIG. 9 is a plot of M-mode correlations averaged over a selected region showing three different lag times. As shown, there is greater decorrelation with increasing lag times at lung motion. Lag greater than 1 appears to provide improved distinction between moving and not moving lung. FIGS. 10A and 1013 are similar illustration but the M-mode correlation is done at lag=2 The plot of FIG. 1013 matches the lag=2 line from FIG. 9B.

Figure 11A:
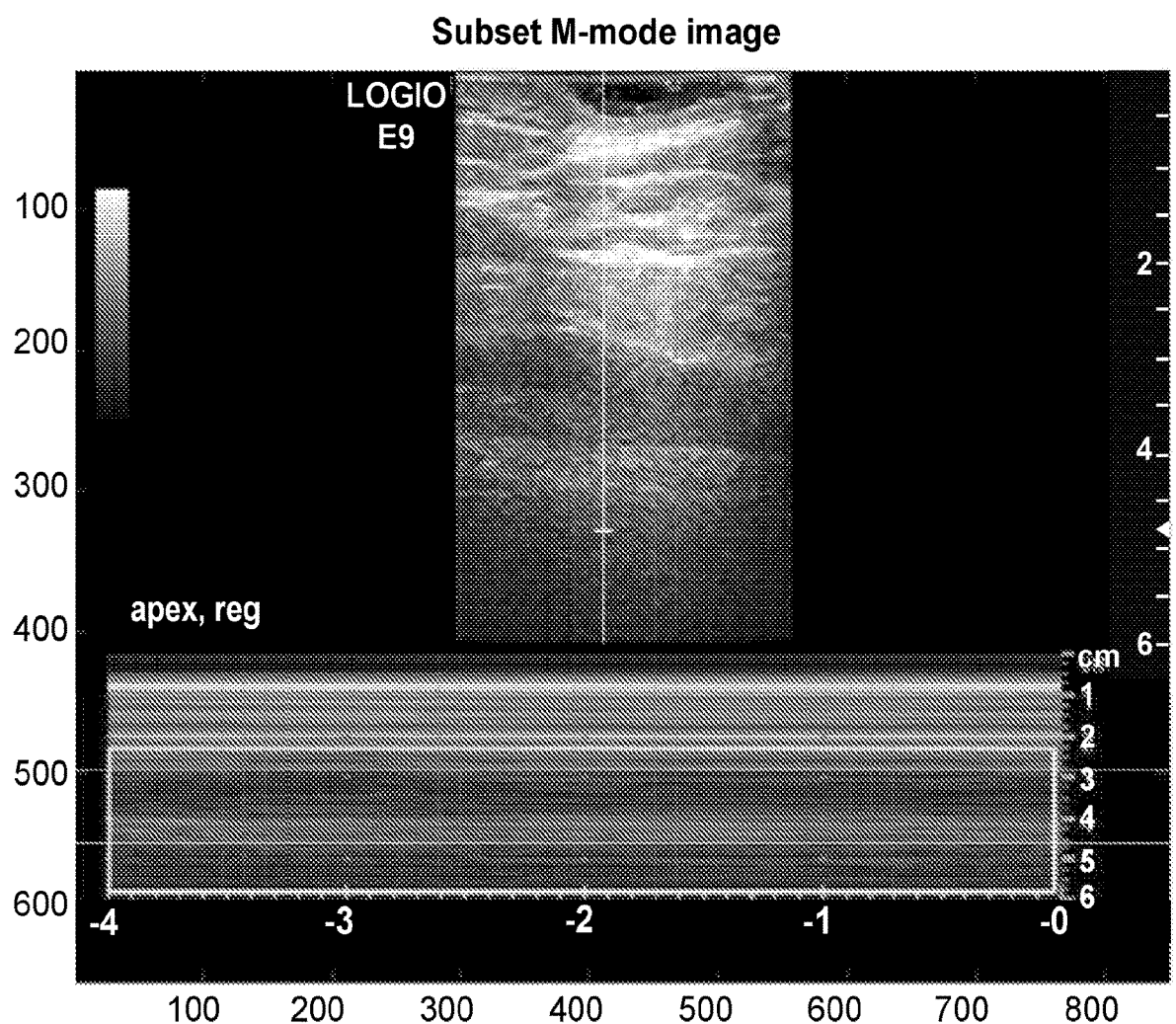
FIGS. 11A and 11B illustrate example DICOM images from the apex during 4 second regular breaths.
Figure 11B:
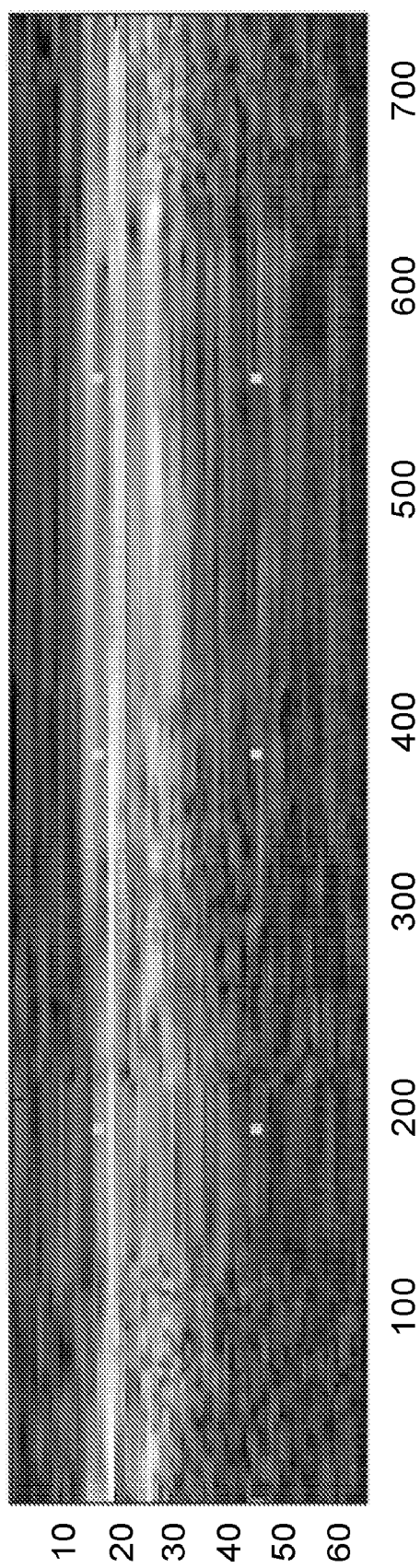
Figure 12A:
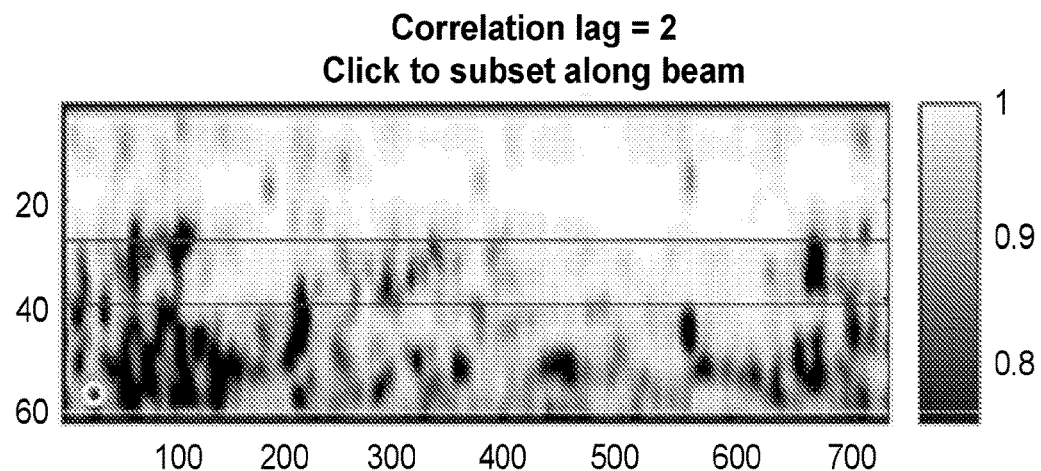
FIGS. 12A-12C illustrate an image and plots corresponding to the example of FIGS. 11A and 11B.
Figure 12B:
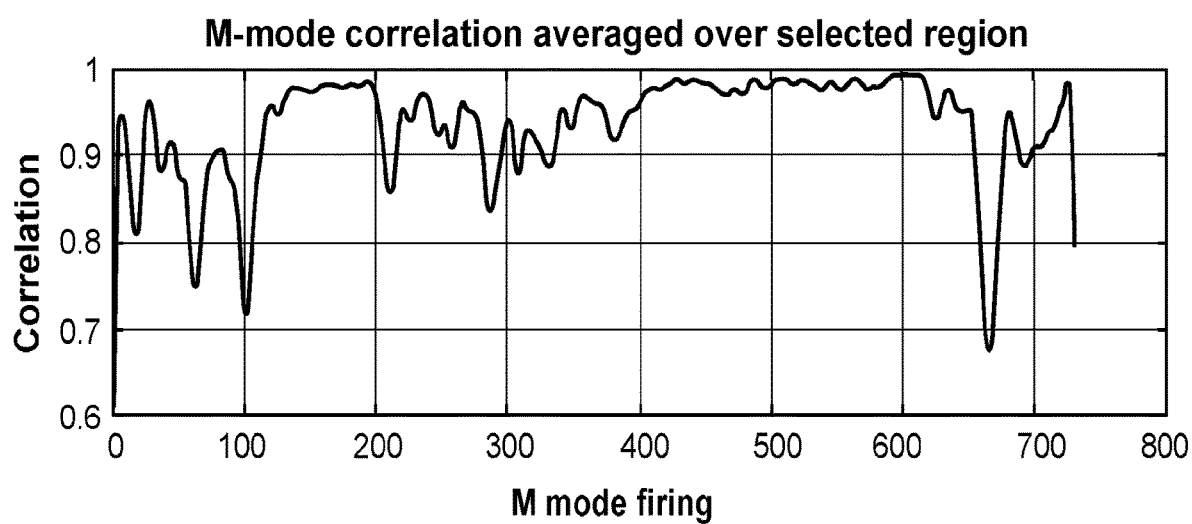
Figure 12C:
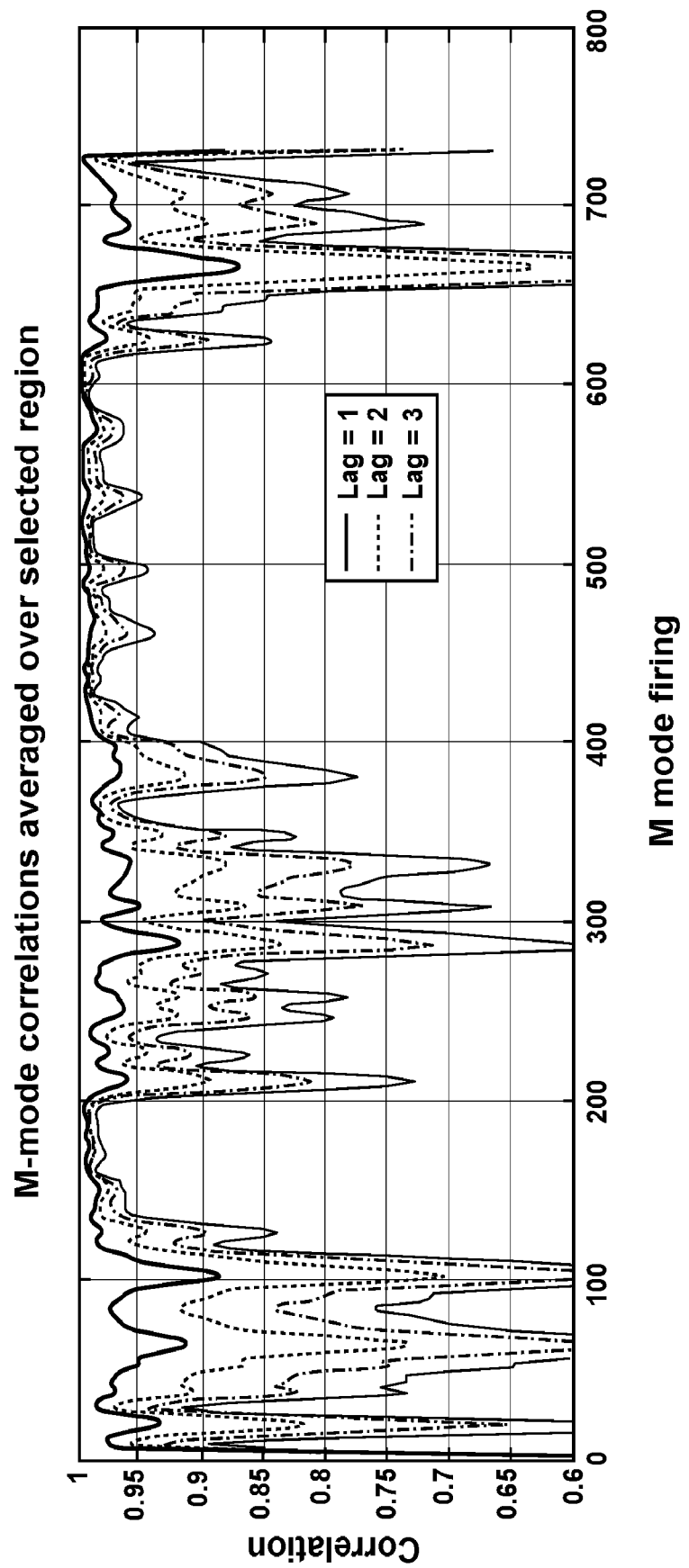

FIGS. 11A and 11B provide M-mode image and M-mode subset taken from the apex of the lung, during a 4 s regular breath. FIGS. 12A-12C illustrate scan depth lines, M-mode correlation averaged over this selected region for Lag 2, and the plot of M-mode correlations averaged at the three Lag times, for the apical portion.

Figure 13A:
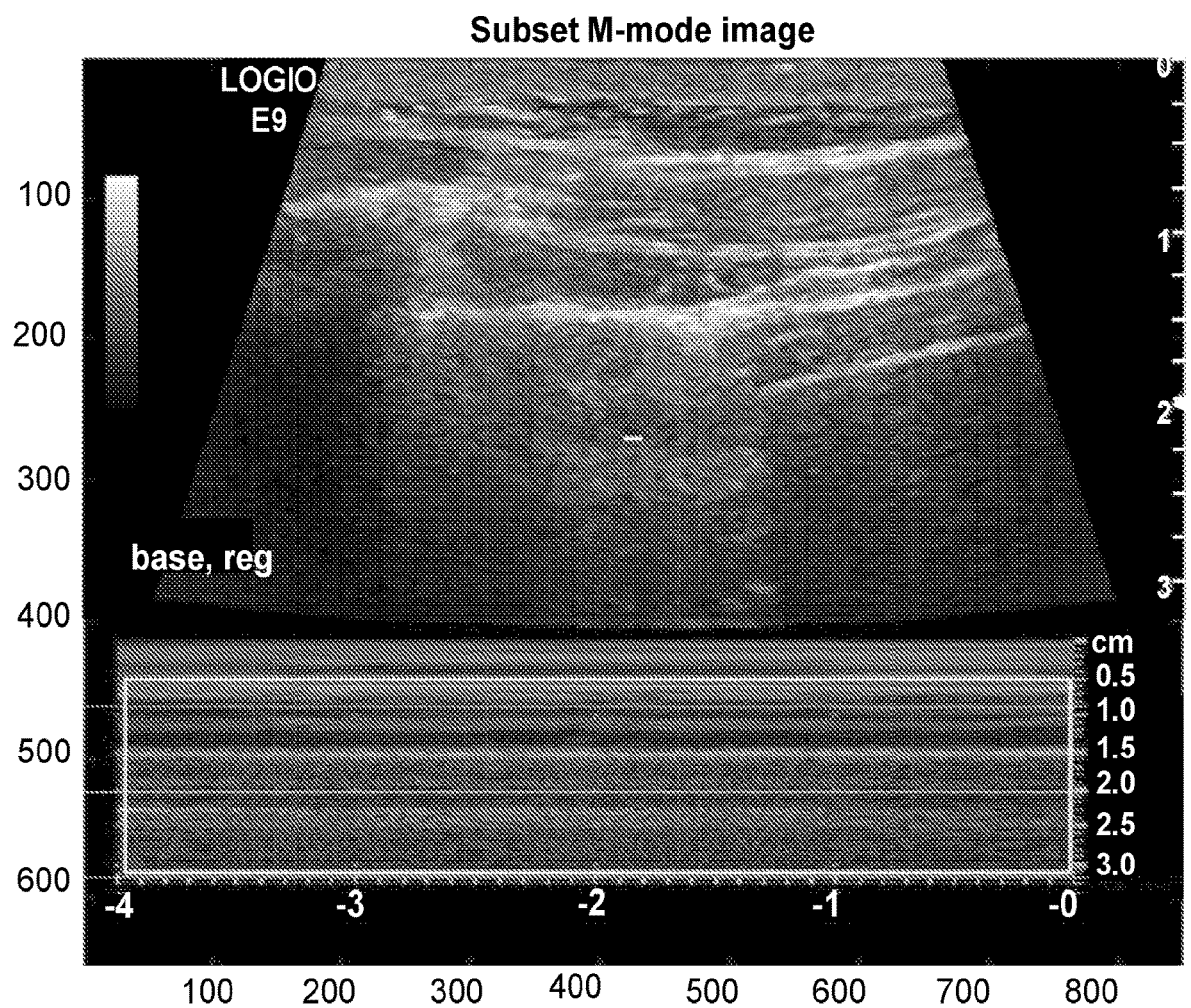
FIGS. 13A and 13B illustrate example DICOM images from the base portion of lung during regular breaths.
Figure 13B:
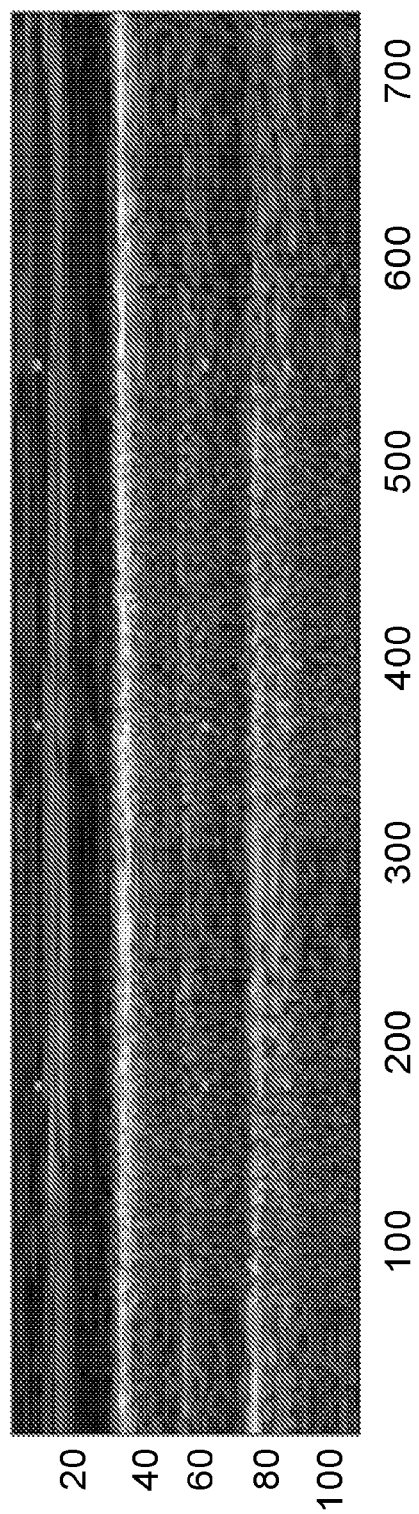
Figure 14A:
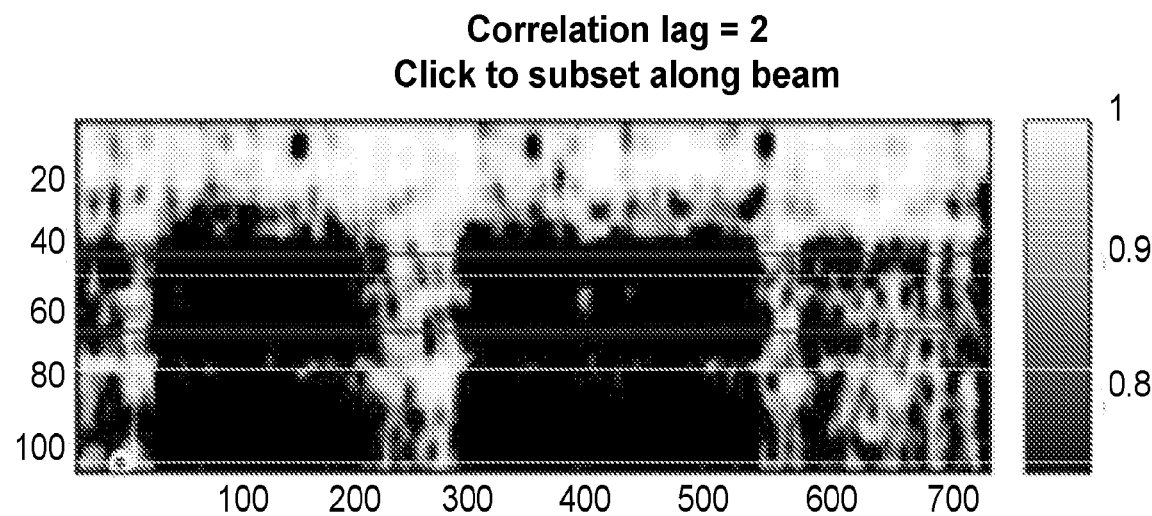
FIGS. 14A-14C illustrate image and plots corresponding to the example of FIGS. 13A and 13B, showing greater decorrelation than the apex and mid level.
Figure 14B:
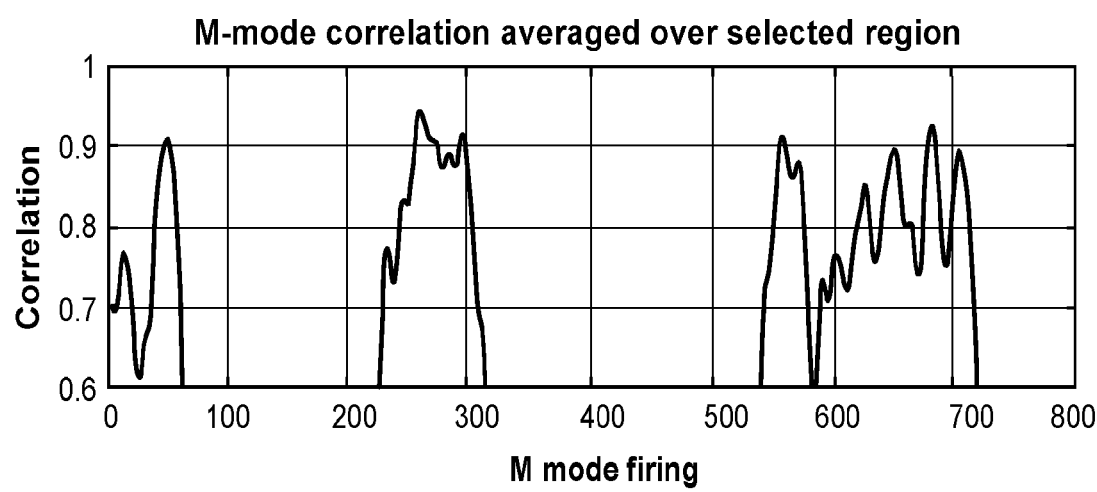
Figure 14C:
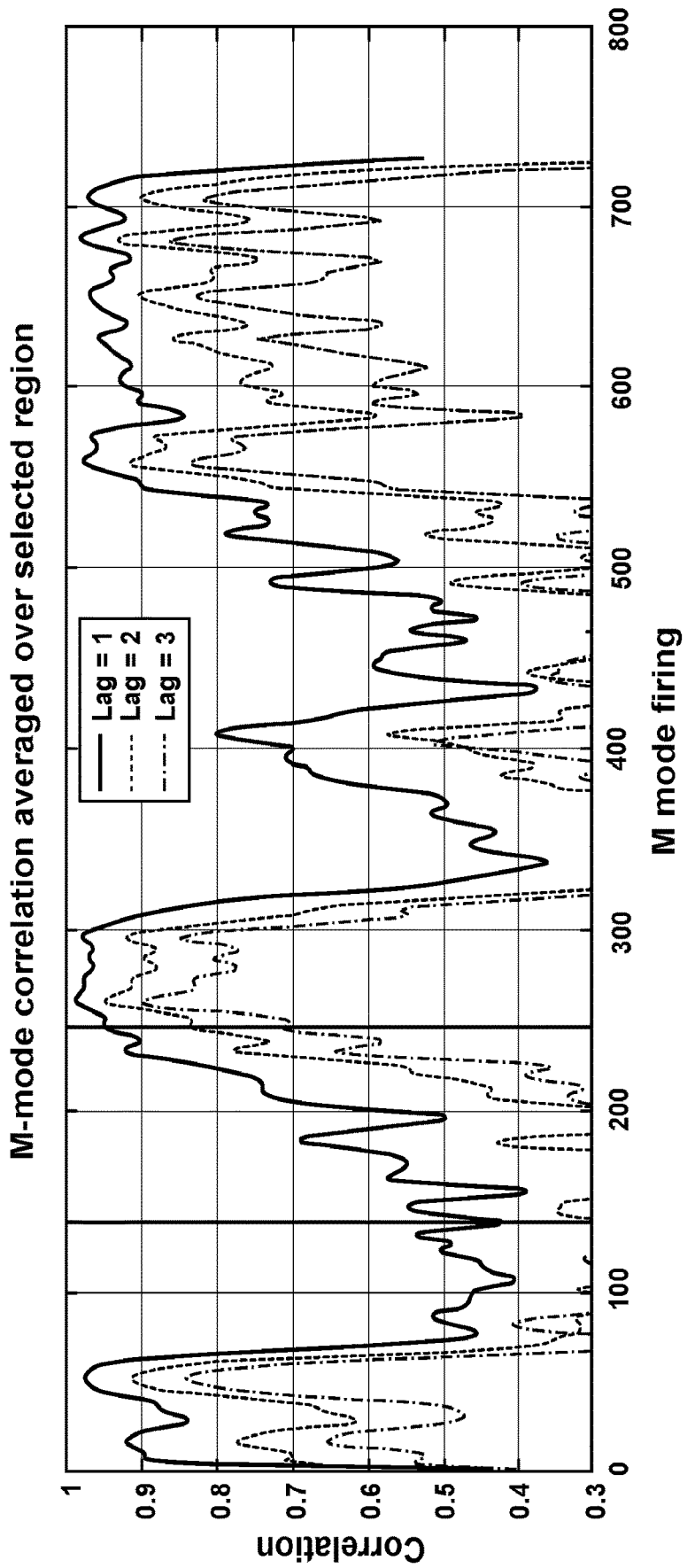

FIGS. 13A and 13B provide M-mode image and M-mode subset taken from the base portion of the lung, during a regular breath. FIGS. 14A-14C illustrates the scan depth lines, M-mode correlation averages, and lag plots for the base of the lung.

Figure 15A:
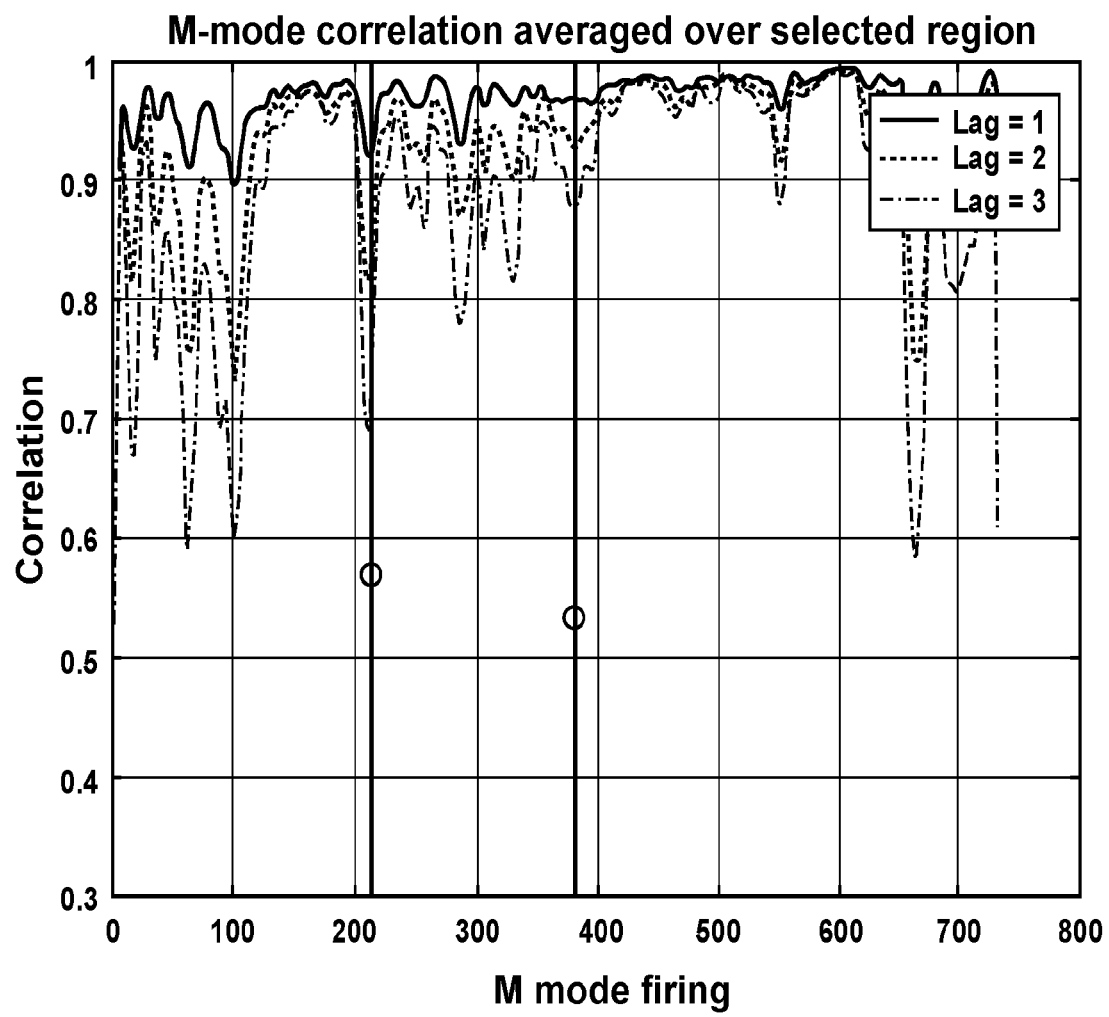
FIGS. 15A-15C are summary plots of lung motion showing average correlation for each lag in this region for regular breath at 4 seconds, at apex, at mid level, and at base, respectively.
Figure 15B:
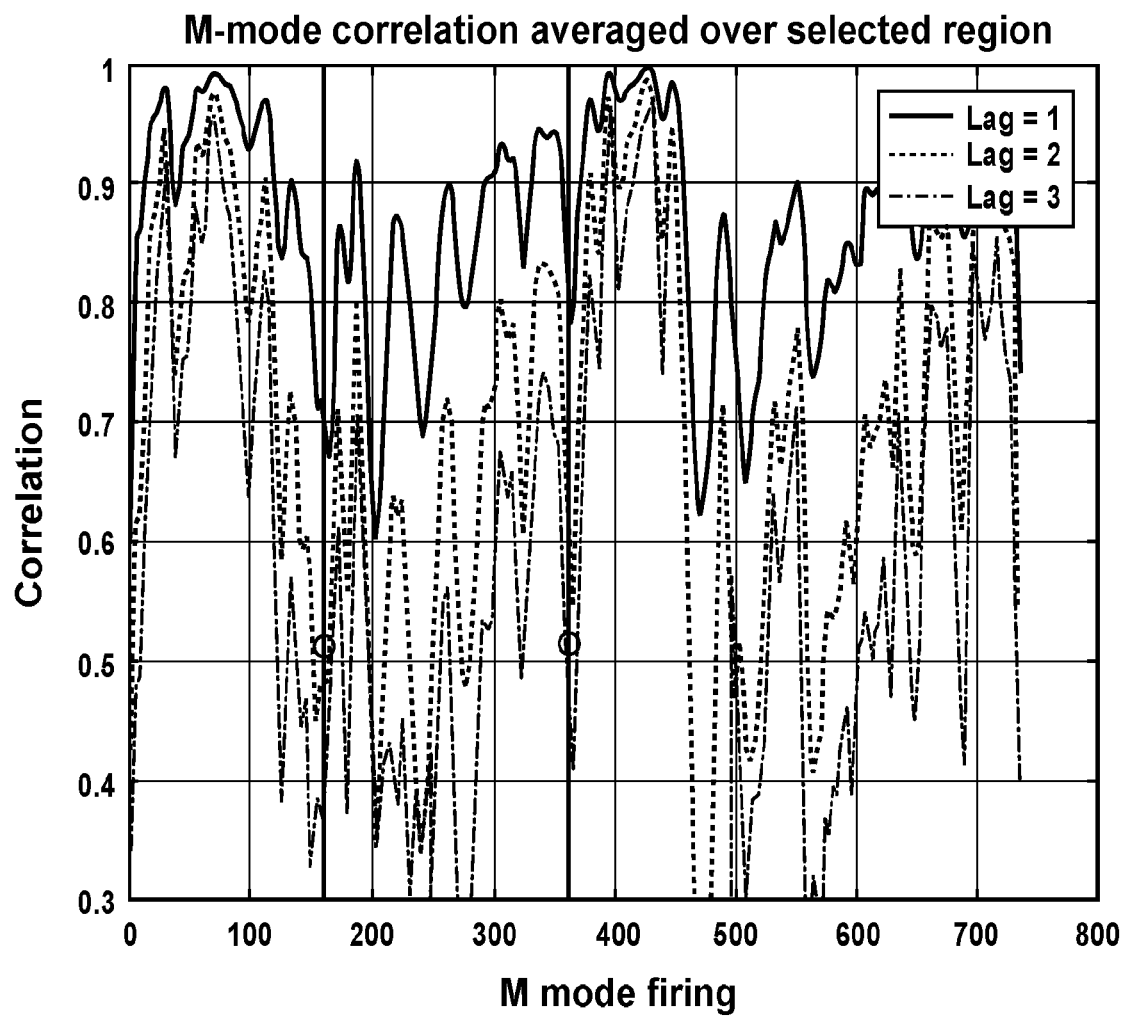
Figure 15C:
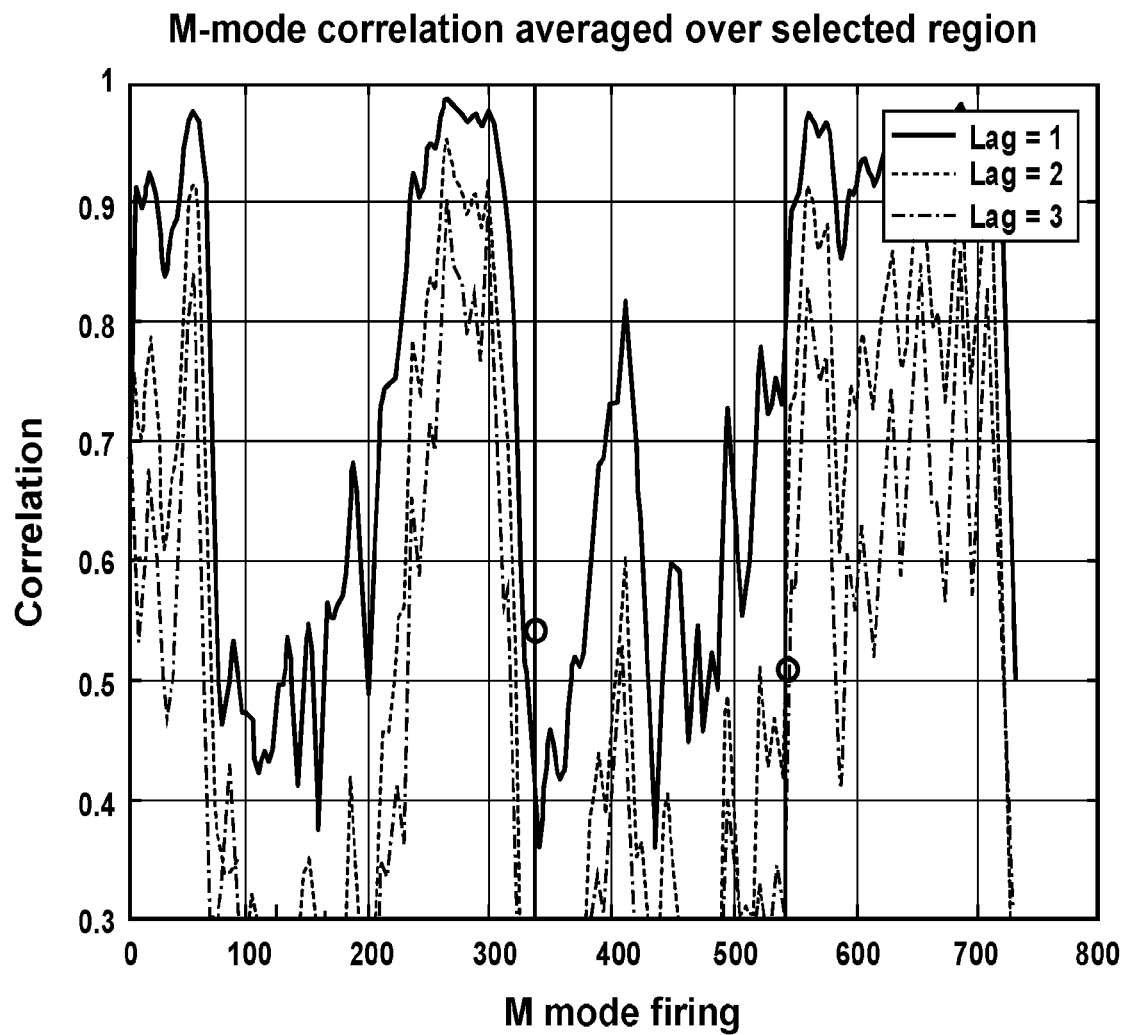

FIG. 15A-15C illustrates different M-mode correlations determined in accordance with an example, from ultrasound image data taken at the apical portion the lung, the mid portion of the lung, and the base of the lung, respectively. As each plot shows, different correlation values are determined for each lag for the selected regions shown.

The present techniques may be used in a variety of applications. For example, functional local lung ventilation assessment can be performed by these techniques, during pulmonary function testing or during artificial ventilation— PEEP evaluation, high frequency ventilation (pediatrics). The techniques may be used to perform post-trauma— pneumothorax assessment, pulmonary hemorrhage. Other examples include Chronic Obstructive Pulmonary Disease assessment—localization/assessment of superficial blebs/bullae. Others include, quantitative pulmonary assessment outside of hospital or clinic, i.e., local pulmonary function monitor that can be carried in an operator's pocket with a smart phone as display and/or uplink.

In clinical settings, the present techniques may be used in emergency scenarios for detecting pulmonary hemorrhage or pneumothoracies and to quantitate the effects of PEEP in pulmonary ventilation—local phenomenon.

Other example, applications include detection of local pneumonias due to differences in local amounts of correlation/decorrelation corresponding to strain difference and recorrelation after long lags. Assessing pulmonary edema and treatment can also be performed by determining correlation and decorrelation properties of the underlying tissue will change. This is consistent with the ultrasound imaging artifacts that are generated with pulmonary edema and used for diagnosis—comets which are largely subjectively assessed.

Further still, the present techniques may be used for changing clinical care by quantitatively assessing PEEP, and using the present techniques to change ventilator setting and subsequent lung damage. Presently, high frequency ventilators have been used, largely in premature children, to minimize lung damage produced by regular mechanical ventilators. However, the tidal volumes used are so small and the changes so rapid that standard global methods of ventilation estimation cannot distinguish among the different varieties of high frequency ventilation. The present techniques are fast enough to make these distinctions. Other examples include use in emergency environments to confirm ventilation or as pneumothorax detector.

The decorrelation results, lung motion determinations, lung ventilation determinations, etc. resulting from the present techniques can be output to a user. In some examples, the operator sees a digital display showing the mean correlation coefficient of the defined region just below the lung surface. The value would be between zero and 1 (or an appropriate color scale for assessment) and the acquisition would be over probably several breaths. In another example, a display is provided showing instantaneous differences in correlation coefficients between two sites over a single breath. These signals would be acquired separately or simultaneously. Knowing the beam correlation widths and distance between sites, this plot could represent the local strain and hence local ventilation. This could provide a similar output to prior lung strain related patent. In other examples, image of correlation coefficients along 1 or 2D samples over time are displayed, for example using 2D or 3D displays.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A method of estimating lung motion, the method comprising:
   capturing, using an ultrasound probe, multiple ultrasound image data at one or more locations of a sample region of tissue;
   comparing, using a processor, the multiple ultrasound image data and determining temporal correlation coefficients between each of the multiple ultrasound image data;
   displaying an image of the sample region of the tissue with the temporal correlation coefficients identified thereby indicating lung motion;
   determining, using the processor, the temporal correlation coefficients at a plurality of lag times; and
   determining, using the processor, an amount of ventilation of the sample region from combining the temporal correlation coefficients at the plurality of lag times by changing the relative magnitudes of decorrelation due to motion/displacement and decorrelation due to shape change/deformation.

2. The method of claim 1, further comprising:
   Collecting, using the processor, the multiple ultrasound image data at a plurality of locations of the sample region; and
   Comparing, using the processor, the multiple ultrasound image data and determining temporal correlation coefficients for each of the plurality of locations of the sample region.

3. The method of claim 1, further comprising:
   Identifying, using input hardware in communication with the processor, a surface of the sample region based on the determined temporal correlation coefficients.

4. The method of claim 1, further comprising:
   identifying, using the processor, an internal structure of the sample region based on the determined temporal correlation coefficients.

5. The method of claim 1, wherein collecting, using the the processor, the multiple ultrasound image data captured at the one or more locations of the sample region of tissue comprises collecting, using the processor, multiple ultrasound image data captured from a 1D ultrasound probe, a 2D ultrasound probe, or a 3D ultrasound probe.

6. The method of claim 1, wherein collecting, using the processor, the multiple ultrasound image data captured at the one or more locations of the sample region of tissue comprises collecting, using the processor, multiple ultrasound image data captured from a plurality of ultrasound probes.

7. The method of claim 1, further comprising: determining, using the processor, the temporal correlation coefficients between each of the multiple ultrasound image data at different successive lag times.

8. The method of claim 1, further comprising: determining from the determined temporal correlation coefficients, using the processor, regions within the sample region that demonstrate no motion.

9. The method of claim 8, wherein the regions of no motion are identified as regions of pneumothoraces.

10. The method of claim 1, further comprising: determining from the determined temporal correlation coefficients, using the processor, 2D lung motion, or 3D lung motion.

11. The method of claim 1, wherein the sample region is a region of a lung.

12. The method of claim 1, further comprising:
    continuously monitoring local respiratory motion at multiple sites across the tissue.

13. The method of claim 1, further comprising:
    determining from the determined temporal correlation coefficients, using a processor, an amount of decorrelation between each of the multiple ultrasound image data;
    identifying, using input hardware in communication with the processor, two sample sites in the tissue spaced by a distance;
    determining, using the processor, displacement differences at the two sample sites based on the amount of decorrelation; and
    from the displacement differences and the distance, determining, using the processor, strain of the tissue over the sample region.

14. The method of claim 1, further comprising:
    Determining, using the processor, decorrelation using two different beam correlation widths; and
    calculating, using the processor, lung displacements and lung shape changes representing ventilation from the two different bema correlation widths.

15. The method of claim 1, further comprising:
    Identifying, using the processor, local displacements and ventilation by determining amounts of decorrelation for two different beam correlation widths or point spread functions.

16. The method of claim 15, further comprising:
    wherein the amounts of amounts of decorrelation for two different beam correlation widths or point spread functions are determined using:

$$TD(i) = \left(\frac{LD}{PSF(i)}\right) + SD$$

$$TD(j) = \left(\frac{LD}{PSF(j)}\right) + SD$$

where TD (i) and TD (j) are the total decorrelation for the $i^{th}$ sampling and $j^{th}$ sampling, respectively, PSF (i) and PSF (j) are the point spread function during the $i^{th}$ sampling and $j^{th}$ sampling, respectively, LD is the lung surface displacement during the sampling period, which is constant, and SD is the shape induced decorrelation during the same period.

17. The method of claim 1, further comprising:
identifying from the determined temporal correlation coefficients, using the processor, decorrelation between first ultrasound image data for the sample region; and
identifying from the determined temporal correlation coefficients, using the processor, re-correlation between second ultrasound image data for the sample region.

18. The method of claim 1, further comprising:
determining, using the processor, the temporal correlation coefficients between each of the multiple ultrasound image data for a surface of the sample region.

19. The method of claim 1, further comprising:
determining, using the processor, the temporal correlation coefficients between each of the multiple ultrasound image data for a portion of the sample region beneath a surface of the sample region.

20. The method of claim 1, further comprising:
determining, using the processor, a mean of the temporal correlation coefficients; and
displaying, using the processor, the mean of the temporal correlation coefficients.

21. The method of claim 1, further comprising:
determining, using the processor, a sum of the temporal correlation coefficients; and
displaying, on a visual display in communication with the processor, the sum of the temporal correlation coefficients.

* * * * *